(12) United States Patent
Gulyani et al.

(10) Patent No.: US 10,808,128 B2
(45) Date of Patent: Oct. 20, 2020

(54) COMPOUNDS AS FLUORESCENT PROBES, SYNTHESIS AND APPLICATIONS THEREOF

(71) Applicant: Institute for Stem Cell Biology and Regenerative Medicine (inStem), Bangalore, Karnataka (IN)

(72) Inventors: Akash Gulyani, Haryana (IN); Sufi Oasim Raja, West Bengal (IN); Gandhi Sivaraman, Tamilnadu (IN)

(73) Assignee: INSTITUTE FOR STEM CELL BIOLOGY AND REGENERATIVE MEDICINE (INSTEM), Bangalore (IN)

(*) Notice: Subject to any disclaimer, the term of this patent is extended or adjusted under 35 U.S.C. 154(b) by 0 days.

(21) Appl. No.: 16/130,448

(22) Filed: Sep. 13, 2018

(65) Prior Publication Data
US 2019/0375941 A1 Dec. 12, 2019

(30) Foreign Application Priority Data
Jun. 11, 2018 (IN) .............................. 201841021840

(51) Int. Cl.
*C09B 23/02* (2006.01)
*C09B 23/01* (2006.01)
*G01N 33/58* (2006.01)

(52) U.S. Cl.
CPC .......... *C09B 23/02* (2013.01); *C09B 23/0066* (2013.01); *G01N 33/582* (2013.01)

(58) Field of Classification Search
None
See application file for complete search history.

(56) References Cited

U.S. PATENT DOCUMENTS 8,877,315 B2 * 11/2014 Yano .................... C07D 401/06
428/64.4

OTHER PUBLICATIONS

Raja et al., "Facile Synthesis of Highly Sensitive, Red-Emitting, Fluorogenic Dye for Microviscosity and Mitochondrial, Imaging in Embryonic Stem Cells", ChemistrySelect, Jun. 12, 2017, 2, pp. 4609-4616, available online at https://onlinelibrary.wiley.com/doi/abs/10.1002/slct.201700463.

* cited by examiner

*Primary Examiner* — Kamal A Saeed
(74) *Attorney, Agent, or Firm* — Hamre, Schumann, Mueller & Larson, P.C.

(57) ABSTRACT

The present disclosure relates to chemical dyes useful for staining and imaging of cells. In particular, the disclosure relates to compound of Formula I, method of preparation thereof, and it's use as a fluorescent probe for staining and/or imaging mitochondria in cells, tissues or animals, resulting in a range of applications including, but not limiting, to sensing local ordering or viscosity of mitochondria, tracking mitochondrial mobility, comparing & evaluating mitochondrial function, local ordering, microviscosity and dynamics. Said dyes have additional advantages including, but not limiting, to low toxicity, longer shelf-life, generate little or no reactive species upon long term light irradiation and do not perturb the functionality of the mitochondria in cells compared to prior art dyes.

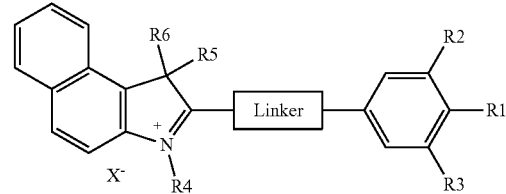

Formula I

11 Claims, 17 Drawing Sheets

HC-1 stained mitochondria of live human pluripotent stem cells

HC-2 stained mitochondria of live human pluripotent stem cells

HC-1 (MS-ESI): 355.2209 (M-I)⁺, Calculated: 355.2169

HC-2 (MS-ESI): 381.4528 (M-I), Calculated: 381.5320

¹H NMR (300 MHz, CDCl₃) δ 8.22 – 8.16 (m, 1H, Ar proton), 8.07 – 7.96 (m, 3H, Ar proton), 7.75 – 7.70 (m, 4H, Ar proton), 7.61 – 7.56 (m, 1H, Ar proton), 7.35 (d, *J* = 15.1 Hz, 1H, Ar proton), 6.82 (d, *J* = 8.3 Hz, 1H, alkene proton), 6.70 (d, *J* = 7.8 Hz, 1H alkene proton,), 3.09 (s, 6H, *N,N'-dimethyl group protons*), 2.06 (s, 6H, methyl protons of phenyl ring),1.51 (s, 3H, Methyl proton of N-methyl ).

$^{13}$C NMR (75 MHz, CDCl$_3$) of HC-1: δ 170.9, 155.0, 153.6, 134.8, 132.9, 131.9, 131.2, 130.2, 128.2, 127.4, 126.4, 122.3, 112.5, 111.7, 110.9, 104.6, 53.4, 40.3, 35.7, 27.2

¹H NMR (300 MHz, CDCl₃) δ 8.17 – 8.01 (m, 4H, Ar proton), 7.76 – 7.69 (m, 3H, Ar proton), 7.61 – 7.36 (m, 5H, Ar proton), 6.82 (d, $J$ = 8.5 Hz, 1H, alkene proton), 6.71 (d, $J$ = 8.0 Hz, 1H, alkene proton), 3.09 (s, 6H *N,N'-dimethyl group protons*), 1.91 (s, 6H, methyl protons of phenyl ring), 1.64 (s, 3H, Methyl proton of N-methyl).

$^{13}$C NMR (75 MHz, CDCl$_3$) of HC-2: δ 175.4, 154.1, 138.9, 137.8, 135.8, 134.7, 131.7, 130.1, 129.1, 128.4,* 128.0, 126.2, 122.1, 121.1, 112.3, 110.7, 105.1, 104.7, 52.4, 44.3, 35.0, 21.9 (*Three carbons are merged)

COMPOUNDS AS FLUORESCENT PROBES, SYNTHESIS AND APPLICATIONS THEREOF

CROSS REFERENCE TO RELATED APPLICATION

This application claims priority to and benefit of Indian Complete Application No. 201841021840, filed Jun. 11, 2018, the disclosure of which is hereby incorporated herein by reference in their entirety.

FIELD OF THE INVENTION

The present disclosure is in the field of chemical sciences and imaging technology. The present disclosure generally relates to chemical dyes useful for staining and imaging of cells. In particular, the disclosure relates to Formula I compounds, method of preparing thereof, and their application as fluorescent probes for staining and/or imaging mitochondria in cells, tissues or animals. Said fluorescent probes also have applications in sensing local ordering or viscosity of mitochondria, tracking mitochondrial mobility, comparing & evaluating mitochondrial function, local ordering and dynamics. The dyes have low toxicity, longer shelf-life, generate little or no reactive species upon long term and repeated light irradiation and do not perturb the functionality of the mitochondria in cells compared to the existing dyes.

BACKGROUND OF THE DISCLOSURE

Probing complex micro-heterogeneous medium including living cells and tissues require a diverse tool-chest of smart sensors that respond to distinct features of the local environment. In this regard, chemical compounds including molecular rotor dyes have been valuable for sensing the local micro-viscosity in the vicinity of the probe. Rotor dyes can respond to micro-viscosity often due to order-sensitive Twisted Intra-molecular Charge Transfer (TICT) states or through mechanisms like inhibition of photoinduced electron transfer (PET) and photo-isomerization. Broadly, 'order-sensing' dyes have been used to probe lipid assemblies as well as cells. Living cells have diverse 'microenvironments', with estimates of cellular micro-viscosity varying from 1-400 cP. While initial studies focused on cytoplasmic micro-viscosity, methods to probe the local environment of specific sub-cellular organelles like the mitochondria and lysosome may be valuable. A common and facile method of live cell mitochondrial imaging is to use cell permeable dyes that stain the mitochondria. There is a considerable demand for small molecule probes for the mitochondria that are easy to use and can provide information on the function, dynamics and the nature of the mitochondria. The existing dyes used for live cell mitochondrial imaging are commonly based on either the Rhodamine or Benzoxazolium or Xanthenolozium scaffold. Though the existing dyes are widely used for staining mitochondria or for measuring mitochondrial potential, they have several disadvantages including the following:

(i) the existing dyes are not optimal for staining sensitive cells like primary cells and stem cells, including embryonic stem cells and induced pluripotent stem cells due to their toxicity and photo-induced damage that they cause. Further, it is known in the art that existing dyes based on Rhodamine scaffold are unsuitable for uniform staining of embryonic stem cell and induced pluripotent stem cells since they are exported out of the cell. This results in uneven staining and under sampling of the mitochondria, (ii) the existing dyes are unsuitable for imaging mitochondria in live cells where functionality is a major concern since these dyes perturb the mitochondrial function, (iii) further, the existing dyes are unsuitable for fast tracking of the mitochondria, due to mitochondrial damage caused by repeated light exposure when these dyes are used. Fast tracking of the mitochondria is important to understand how the mitochondria moves and segregates in the cell. This segregation and movement is linked to the cell state, energetics and function but currently there is no method to obtain this information using cell permeable dyes. There is now growing evidence that understanding mitochondrial dynamics is linked to disease pathologies, (iv) furthermore, tracking of mitochondria in stem cells with existing dyes causes differentiation of stem cells through reactive oxygen species (ROS) generation, making them unsuitable for repeated and rapid imaging of stem cells.

Currently, the common parameter used for describing mitochondrial function is mitochondrial potential. While mitochondrial potential is important, it does not fully describe the mitochondrial state and function. There is evidence that mitochondria with similar potential are processed very differently in the cell, depending on other parameters. These mitochondrial parameters are critical in multiple disease pathologies but existing dyes are inadequate to describe these features. In several cases, mitochondrial potential is insufficient to distinguish different mitochondrial states. These distinct states are important in disease conditions. For instance, it can determine cell death or survival.

Therefore, there is a continuous need in the art to develop simple, long wavelength probes that can efficiently report changes in the mitochondrial microenvironment, especially the local ordering (micro-viscosity). Long wavelength probes reduce imaging noise and allow deep tissue imaging, but often require complex synthesis. Easily accessible, sensitive, chemically diverse and long wavelength probes would enable comprehensive imaging of the complex mitochondrial microenvironment. Accordingly, the present disclosure aims to address the above needs of the prior art.

SUMMARY OF THE DISCLOSURE

The present disclosure provides a compound of the following structure:

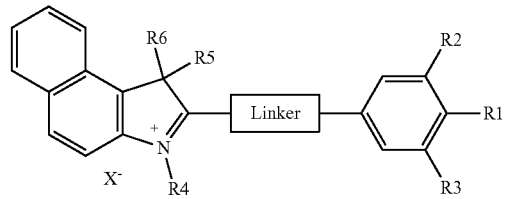

Formula I wherein,
'R1' is selected from a group consisting of hydrogen, dialkyl amino, diaryl amino and alkoxy;
'R2', 'R3', 'R4', 'R5' and 'R6' are individually selected from a group consisting of hydrogen, alkoxy and alkyl;
'X' is selected from a group consisting of I, Cl, Br and F; and
'Linker' is selected from a group consisting of alkenylene moiety (—CH=CH—) and alkadienyl group (—CH=CH—CH=CH—).

A process for preparing the compound of Formula I as defined above, comprising of reacting a compound of Formula III with a substituted or unsubstituted aldehyde derivative in presence of anhydrous ethanol and piperidine under reflux conditions for a time period ranging from about 2 hours to about 3 hours,
wherein the compound of Formula III is

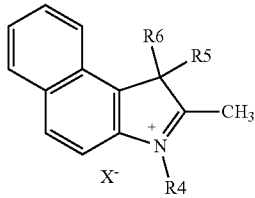

Formula III wherein
'R4', 'R5' and 'R6' are individually selected from a group consisting of hydrogen, alkoxy and alkyl; and
'X' is selected from a group consisting of I, Cl, Br and F.

Use of the compound of Formula I as defined above as a fluorescent probe in applications selected from a group comprising staining and imaging mitochondria in eukaryotic cells, tissues or animals, sensing local ordering or viscosity of mitochondria in eukaryotic cells, tissues or animals, tracking mitochondrial mobility in eukaryotic cells, tissues or animals, comparing and evaluating mitochondrial function, order and dynamics in eukaryotic cells, tissues or animals, and combinations thereof.

A method of imaging mitochondria in eukaryotic cells, tissues or animals comprising: contacting the eukaryotic cells, tissues or animals with the compound of Formula I as defined above to stain the mitochondria and imaging the mitochondria.

DETAILED DESCRIPTION OF THE DISCLOSURE

Figures 1A, 1B, 1C, 1D, 1E:
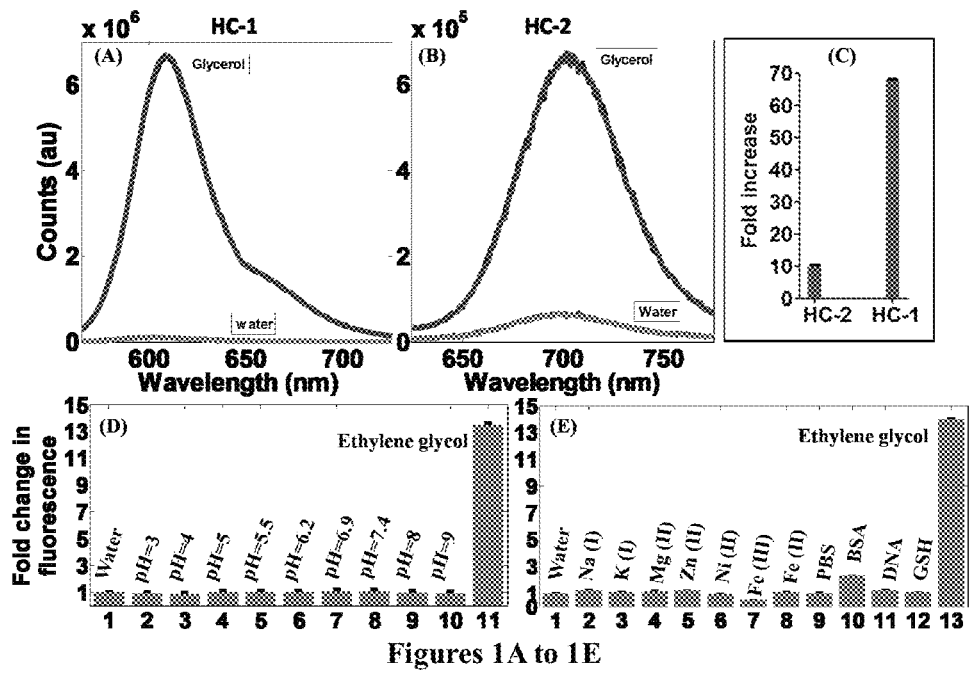
FIGS. 1A to 1E: Steady state fluorescence spectra of HC-1 (A) and HC-2 (B) in water and glycerol (dye concentration 1 mM). (C) Shows the fold-increase in fluorescence of HC-1 and HC-2 in glycerol compared to water. (D) Shows the fold change in fluorescence of HC-1 compared to the fluorescence in water in buffers of different pH specified in the inset. Fold change in fluorescence in ethylene glycol is provided as reference for comparison. (E) Shows the effect of ions (10 mM), serum proteins (1 mg-ml$^{-1}$), plasmid DNA (5 mg-m$^{-1}$) and glutathione (GSH), 10 mM on HC-1 fluorescence. X-axis is the sample numbers indicated in the inset. Y-axis is the fold increase in fluorescence of HC-1 compared to fluorescence in water.

While many of the following terms are believed to be understood by one of ordinary skill in the art, the following definitions are set forth to facilitate better explanation of the presently disclosed subject matter.

The terms 'probe' and 'dye' are used interchangeably herein.

The term "a" or "an" refers to one or more of that entity. As such, the terms "a" (or "an"), "one or more" and "at least one" are used interchangeably herein. In addition, reference to "a compound" by the indefinite article "a" or "an" does not exclude the possibility that more than one of the compounds is present, unless the context clearly requires that there is one and only one of the compound.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

"Alkyl" or "alkyl group" refers to a fully saturated, straight or branched hydrocarbon chain radical having from one to twelve carbon atoms, and which is attached to the rest of the molecule by a single bond. Alkyls consisting of any number of carbon atoms from 1 to 12 are included. An alkyl consisting of up to 12 carbon atoms is a C1-C12 alkyl, an alkyl consisting of up to 10 carbon atoms is a C1-C10 alkyl, an alkyl consisting of up to 6 carbon atoms is a C1-C6 alkyl and an alkyl consisting of up to 5 carbon atoms is a C1-C5 alkyl. A C1-C6 alkyl includes C6 alkyls, C5 alkyls, C4 alkyls, C3 alkyls, C2 alkyls and C1 alkyl (i.e., methyl). Non-limiting examples of C1-C12 alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a C2-C12 alkenyl, an alkenyl comprising up to 10 carbon atoms is a C2-C10 alkenyl, an alkenyl group comprising up to 6 carbon atoms is a C2-C6 alkenyl and an alkenyl comprising up to 5 carbon atoms is a C2-C5 alkenyl. A C2-C6 alkenyl includes all moieties described above for C2-C5 alkenyls but also includes C6 alkenyls. Unless stated otherwise specifically in the specification, an alkyl group can be optionally substituted.

"alkenylene moiety" refers to "—CH═CH—".

"Alkoxy" refers to a radical of the formula OR where R is an alkyl, wherein said alkyl refers to a fully saturated, straight or branched hydrocarbon chain radical having from one to twelve carbon atoms, and which is attached to the rest of the molecule by a single bond. Alkyls consisting of any number of carbon atoms from 1 to 12 are included. An alkyl consisting of up to 12 carbon atoms is a C1-C12 alkyl, an alkyl consisting of up to 10 carbon atoms is a C1-C10 alkyl, an alkyl consisting of up to 6 carbon atoms is a C1-C6 alkyl and an alkyl consisting of up to 5 carbon atoms is a C1-C5 alkyl. A C1-C6 alkyl includes C6 alkyls, C5 alkyls, C4 alkyls, C3 alkyls, C2 alkyls and C1 alkyl (i.e., methyl). Non-limiting examples of C1-C12 alkyl include methyl, ethyl, n-propyl, propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Dialkylamino" refers to a radical of the formula —NR$^1$R$^2$ where each R$^1$ and R$^2$ ae, independently, an alkyl, alkenyl or alkynyl radical as defined above. In some embodiments, R$^1$ and R$^2$ may be the same alkyl group. Unless stated otherwise specifically in the specification, an alkylamino group can be optionally substituted.

"Aryl" refers to a hydrocarbon ring system radical consisting of hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from anthracene, benzene, naphthalene, phenanthrene and triphenylene. Unless stated otherwise specifically in the specification, the term "aryl" is meant to include aryl radicals that are optionally substituted.

"Diarylamino" refers to substituted or unsubstituted diphenylamino radical.

"Alkadienyl" refers to a radical alkadienyl C-4 to C-10 and includes, but not limited to 1,3-butadienyl radical "—CH═CH—CH═CH—", 1,4 hexadienyl radical, and similar radicals.

The term "substituted" used herein means any of the above groups (i.e., alkyl, alkylene, alkenyl, alkenylene, alkynyl, alkynylene, alkoxy, alkylamino, alkylcarbonyl, aryl, haloalkyl, heterocyclyl, heteroaryl and/or N-heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. In addition, each of the foregoing substituents can also be optionally substituted with one or more of the above substituents.

The present disclosure aims at addressing the above mentioned drawbacks by providing efficient chemical fluorescent probes having wide range of applications. In particular, the present disclosure provides a compound of the following structure:

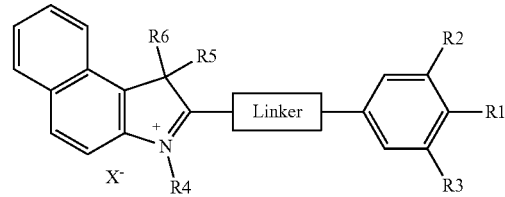

Formula I wherein,
'R1' is selected from a group consisting of hydrogen, dialkyl amino, diaryl amino and alkoxy;
'R2', 'R3', 'R4', 'R5' and 'R6' are individually selected from a group consisting of hydrogen, alkoxy and alkyl;
'X' is selected from a group consisting of I, Cl, Br and F; and
'Linker' is selected from a group consisting of alkenylene moiety (—CH═CH—), alkadienyl group (—CH═CH—CH═CH—).

The present disclosure further provides a compound of the following structure:

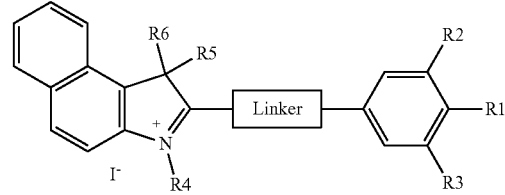

Formula II

| Formula II compounds | R1 | R2 | R3 | R4 | R5 | R6 | Linker |
|---|---|---|---|---|---|---|---|
| HC-1 | —N(CH3)$_2$ | —H | —H | —CH3 | —CH3 | —CH3 | —CH═CH— |
| HC-2 | —N(CH3)$_2$ | —H | —H | —CH3 | —CH3 | —CH3 | —CH═CH—CH═CH— |
| HC-3 | —N(Ph)$_2$ | —H | —H | —CH3 | —CH3 | —CH3 | —CH═CH— |
| HC-4 | —O—CH3 | —H | —H | —CH3 | —CH3 | —CH3 | —CH═CH— |

-continued

| Formula II compounds | R1 | R2 | R3 | R4 | R5 | R6 | Linker |
|---|---|---|---|---|---|---|---|
| HC-5 | —H | —O—CH3 | —O—CH3 | —CH3 | —CH3 | —CH3 | —CH=CH— |
| HC-6 | —O—CH3 | —O—CH3 | —O—CH3 | —CH3 | —CH3 | —CH3 | —CH=CH— |
| HC-7 | —N(CH3)$_2$ | —H | —H | —C$_2$H$_5$ | —CH3 | —CH3 | —CH=CH— |
| HC-8 | —N(CH3)$_2$ | —H | —H | —C$_6$H$_{13}$ | —CH3 | —CH3 | —CH=CH— |
| HC-9 | —O—CH3 | —H | —H | —C$_6$H$_{13}$ | —CH3 | —CH3 | —CH=CH— |
| HC-10 | —O—C$_6$H$_{13}$ | —H | —H | —CH$_3$ | —CH3 | —CH3 | —CH=CH— |
| HC-11 | —O—C$_{10}$H$_{21}$ | —H | —H | —CH$_3$ | —CH3 | —CH3 | —CH=CH— |
| HC-12 | —O—C$_{12}$H$_{25}$ | —H | —H | —CH$_3$ | —CH3 | —CH3 | —CH=CH— |
| HC-13 | —N(CH3)$_2$ | —H | —H | —C$_6$H$_{13}$ | —CH3 | —CH3 | —CH=CH—CH=CH— |

In an embodiment of the present disclosure, the compounds of Formula I or Formula II are selected from:

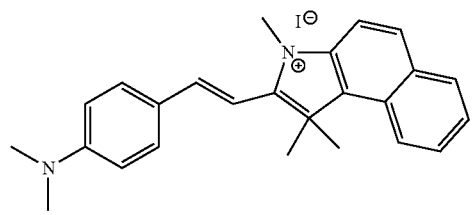

(E)-2-(4-(Dimethylamino)styryl)-1,1,3-trimethyl-1H-benzo[e]indol-3-ium iodide [HC-1];

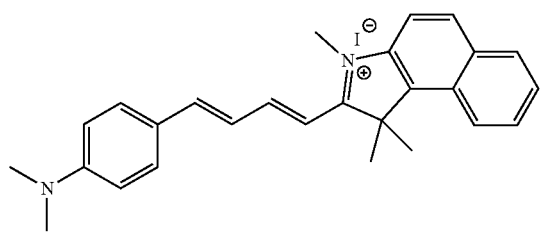 [SMILES: CN(C)c1ccc(/C=C/C=C/C2=[N+](C)c3ccc4ccccc4c3C2(C)C)cc1 ; [I-]]

2-((1E,3E)-4-(4-(Dimethylamino)phenyl)buta-1,3-dien-1-yl)-1,1,3-trimethyl-1H-benzo[e]indol-3-ium iodide [HC-2];

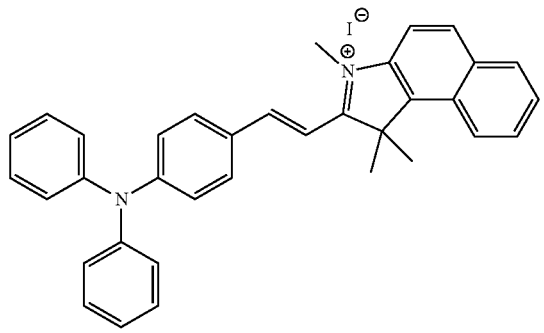

(E)-2-(4-(diphenylamino)styryl)-1,1,3-trimethyl-1H-benzo[e]indol-3-ium iodide [HC-3];

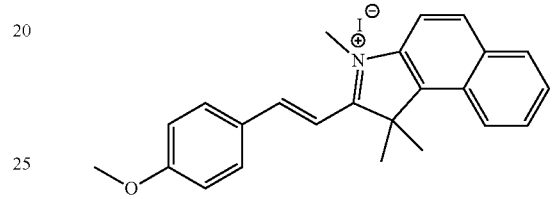

(E)-2-(4-methoxystyryl)-1,1,3-trimethyl-1H-benzo[e]indol-3-ium iodide [HC-4];

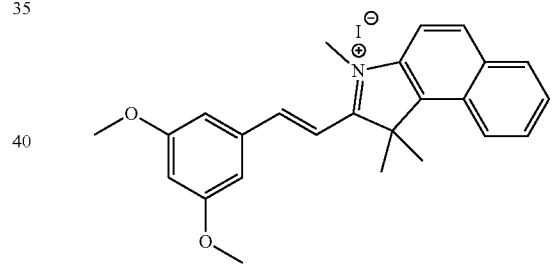

(E)-2-(3,5-dimethoxystyryl)-1,1,3-trimethyl-1H-benzo[e]indol-3-ium iodide [HC-5];

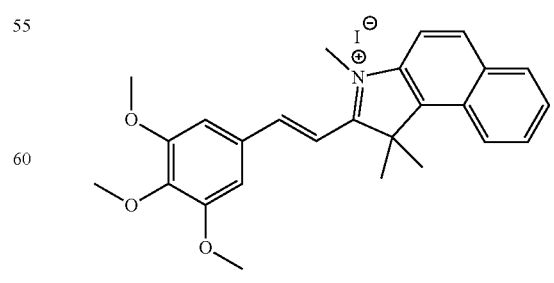

(E)-1,1,3-trimethyl-2-(3,4,5-trimethoxystyryl)-1H-benzo[e]indol-3-ium iodide [HC-6];

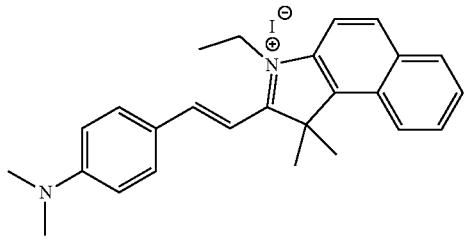

(E)-2-(4-(dimethylamino)styryl)-3-ethyl-1,1-dimethyl-1H-benzo[e]indol-3-ium iodide [HC-7];

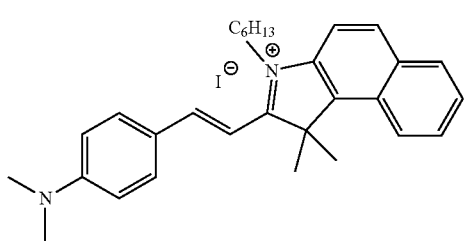

(E)-2-(4-(dimethylamino)styryl)-3-hexyl-1,1-dimethyl-1H-benzo[e]indol-3-ium iodide [HC-8];

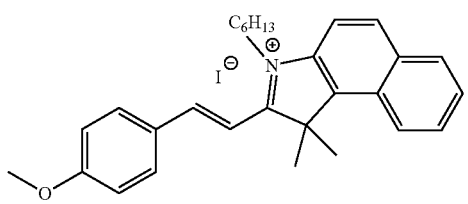

(E)-3-hexyl-2-(4-methoxystyryl)-1,1-dimethyl-1H-benzo[e]indol-3-ium iodide [HC-9];

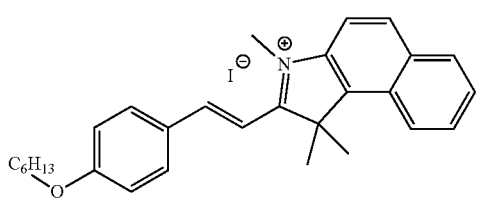

(E)-2-(4-(hexyloxy)styryl)-1,1,3-trimethyl-1H-benzo[e]indol-3-ium iodide [HC-10];

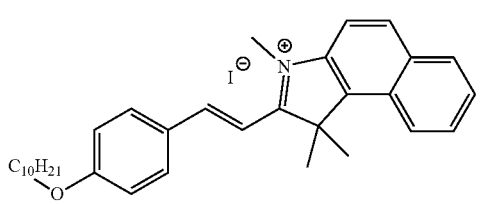

(E)-2-(4-(decyloxy)styryl)-1,1,3-trimethyl-1H-benzo[e]indol-3-ium iodide [HC-11];

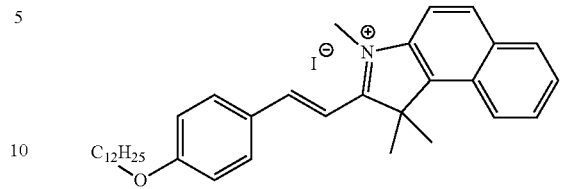

(E)-2-(4-(dodecyloxy)styryl)-1,1,3-trimethyl-1H-benzo[e]indol-3-ium iodide [HC-12]; or

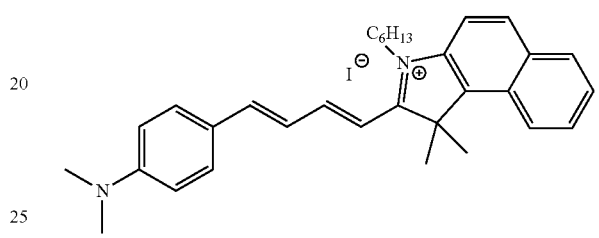

2-((1E,3E)-4-(4-(dimethylamino)phenyl)buta-1,3-dien-1-yl)-3-hexyl-1,1-dimethyl-1H-benzo[e]indol-3-ium iodide [HC-13].

The present disclosure also provides a process for the preparation of the compound of Formula I as defined above, comprising of the step of reacting a compound of Formula III with a substituted or unsubstituted aldehyde derivative in presence of anhydrous ethanol and piperidine under reflux conditions for a time period ranging from about 2 hours to about 3 hours, wherein the compound of Formula III is:

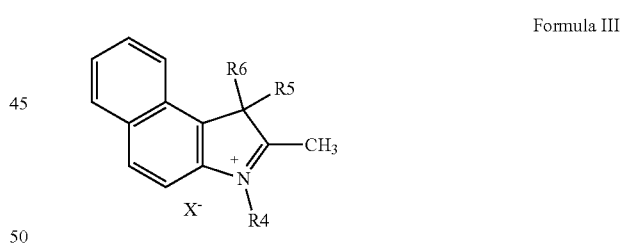

Formula III wherein

'R4', 'R5' and 'R6' are individually selected from a group consisting of hydrogen, alkoxy and alkyl; and 'X' is selected from a group consisting of I, Cl, Br and F.

The present disclosure also provides a process for the preparation of the compound of Formula I as defined above, essentially consisting of the step of reacting a compound of Formula III with a substituted or unsubstituted aldehyde derivative in presence of anhydrous ethanol and piperidine under reflux conditions for a time period ranging from about 2 hours to about 3 hours, wherein the compound of Formula III is Formula III

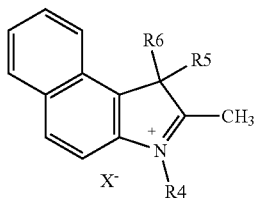

wherein

'R4', 'R5' and 'R6' are individually selected from a group consisting of hydrogen, alkoxy and alkyl; and 'X' is selected from a group consisting of I, Cl, Br and F.

In a preferred embodiment of the present disclosure, the compound of formula III is selected from a group consisting of 1,1,2-trimethyl-1H-benzo[e]indolium iodide, 3-ethyl-1,1,2-trimethyl-1H-benz[e]indolium iodide and 3-hexyl-1,1,2-trimethyl-1H-benzo[e]indol-3-ium iodide.

In another preferred embodiment of the present disclosure, the substituted or unsubstituted aldehyde derivative is selected from a group consisting of 4-(dimethylamino)benzaldehyde, 4-(diphenylamino)benzaldehyde, 4-methoxybenzaldehyde, 3,5-dimethoxybenzaldehyde, 3,4,5-trimethoxy benzaldehyde, 4-hexyloxybenzaldehyde, 4-decyloxybenzaldehyde, 4-dodecyloxybenzaldehyde and 4-(dimethylamino)cinnamaldehyde.

In another embodiment of the present disclosure, the process further consisting of isolation, purification or a combination thereof of the product. In yet another embodiment, said isolation and purification is carried out by acts selected from a group consisting of addition of solvent, washing with solvent, cooling, quenching, filtration, extraction, chromatography and combinations thereof.

In an exemplary embodiment of the present disclosure, HC-1 is prepared by a process essentially consisting of the step of reacting 1,1,2-trimethyl-1H-benzo[e]indolium iodide with 4-(dimethylamino)benzaldehyde in presence of anhydrous ethanol and piperidine under reflux conditions for a time period ranging from about 2 hours to about 3 hours.

In another exemplary embodiment of the present disclosure, HC-2 is prepared by a process essentially consisting of the step of reacting 1,1,2-trimethyl-1H-benzo[e]indolium iodide with 4-(dimethylamino)cinnamaldehyde in presence of anhydrous ethanol and piperidine under reflux conditions for a time period ranging from about 2 hours to about 3 hours.

In yet another embodiment of the present disclosure, the process for preparing compound of Formula I further comprises the step of cooling the reaction mixture.

In yet another embodiment of the present disclosure, the process for preparing compound of Formula I further comprises the step of purification of the product by chromatography after cooling the reaction mixture.

The present disclosure provides use of the above defined compound of Formula I as a mitochondrial fluorescent probe/dye.

In an embodiment of the present disclosure, the compound of Formula I is used as a cellular/mitochondrial micro-viscosity probe.

In another embodiment of the present disclosure, the compound of Formula I is used as a probe for intracellular staining or mitochondrial staining.

In yet another embodiment of the present disclosure, the compound of Formula I is used as a probe for cell imaging or mitochondrial imaging. In an exemplary embodiment, the cells are live eukaryotic cells.

The present disclosure further provides use of the above defined compound of Formula I as a fluorescent probe for staining and/or imaging mitochondria in cells, tissues or animals, sensing local ordering or viscosity of mitochondria in cells, tissues or animals, tracking mitochondrial mobility in cells, tissues or animals, comparing and evaluating mitochondrial function, order and dynamics in cells, tissues or animals, and combinations thereof.

The present disclosure further provides a method of using the above defined compound of Formula I as a fluorescent probe for staining and/or imaging mitochondria in cells, tissues or animals, sensing local ordering or viscosity of mitochondria in cells, tissues or animals, tracking mitochondrial mobility in cells, tissues or animals, comparing and evaluating mitochondrial function, order and dynamics in cells, tissues or animals, and combinations thereof.

In an embodiment of the present disclosure, the method of using the compound of Formula I as a fluorescent probe for applications selected from a group comprising staining and imaging mitochondria in cells, sensing local ordering or viscosity of mitochondria in cells, tracking mitochondrial mobility in cells, or comparing and evaluating mitochondrial function, order and dynamics in cells, comprises:

a) contacting the cells with the compound of Formula I by adding a cell culture medium containing the compound to the cells, b) incubating the cells for a time-period ranging from about 5 minutes to about 48 hours, wherein the incubation time-period depends on the cell type/cell sample, c) optionally, washing off the excess compound and adding a fresh cell culture media, to obtain cells with stained mitochondria, and d) imaging the stained cells by fluorescence microscope and studying/analyzing local ordering or micro-viscosity of mitochondria in cells, tracking mitochondrial mobility in cells, comparing and evaluating mitochondrial function, order and dynamics in cells, or any combinations thereof.

The present disclosure also provides a method of staining and/or imaging mitochondria in cells, tissues or animals comprising contacting the eukaryotic cells, tissues or animals with the compound of Formula I as defined above to stain the mitochondria, and imaging the mitochondria.

The present disclosure also provides a method of staining and/or imaging mitochondria in cells, tissues or animals essentially consisting of contacting the eukaryotic cells, tissues or animals with the compound of Formula I as defined above to stain the mitochondria, and imaging the mitochondria.

In an embodiment of the present disclosure, the imaging is fluorescence imaging.

In another embodiment of the present disclosure, the method of staining and/or imaging further comprises sensing local ordering or viscosity of the mitochondria, tracking the mitochondrial mobility, and dynamics or combinations thereof.

In yet another embodiment of the present disclosure, the sensing of said local ordering or viscosity is performed by measuring fluorescence intensity, fluorescence lifetime, or a combination thereof.

In still another embodiment of the present disclosure, the method of staining and/or imaging further comprises evaluating mitochondrial function by said sensing of the local ordering or viscosity of the mitochondria.

In still another embodiment of the present disclosure, the tracking of mitochondrial mobility and dynamics is performed by time-lapse imaging using repeat photo illumination.

In still another embodiment of the present disclosure, evaluation of a state, a function, or a combination thereof of the cells or tissues can be achieved by mitochondrial imaging.

In still another embodiment, the present disclosure further comprises identifying or screening a disease condition by evaluating changes in said state, function or a combination thereof of said cells or tissues by mitochondrial imaging.

In another embodiment of the present disclosure, the method of imaging mitochondria in cells comprising:
  a) contacting the cells with the compound of Formula I by adding a cell culture medium containing the compound to the cells,
  b) incubating the cells for a time-period ranging from about 5 minutes to about 48 hours,
  c) optionally, washing off the excess compound and adding a fresh cell culture media, to obtain stained cells, and
  d) imaging the stained cells by fluorescence microscope.

In an embodiment of the present disclosure, the cells are eukaryotic cells. In an exemplary embodiment, the eukaryotic cells are live eukaryotic cells.

In another embodiment of the present disclosure, the eukaryotic cells are live primary cells, human pluripotent stem cells (hPSCs) or a combination thereof.

In yet another embodiment of the present disclosure, the eukaryotic cells are from human origin, mouse origin or any other animal origin.

In a preferred embodiment of the present disclosure, the eukaryotic cells are selected from a group consisting of cells in culture, cultured cells, cells from tissue and combinations thereof.

In a preferred embodiment of the present disclosure, the live primary cells are selected from a group consisting of fibroblast cells, stem cells and a combination thereof. In an exemplary embodiment of the present disclosure, the stem cells are selected from a group consisting of embryonic stem cells, adult stem cells and a combination thereof. In another exemplary embodiment of the present disclosure, the pluripotent stem cells (PSCs) are selected from a group consisting of human pluripotent stem cells (hPSCs), mouse embryonic stem cells (mESCs), induced human pluripotent stem cells from any other animal and combinations thereof.

In an embodiment of the present disclosure, the animal is human or mouse.

In an embodiment, the present disclosure provides a method of using the above-defined compound of Formula I for evaluating mitochondrial function and dynamics in cellular models of human or animal diseases. In another embodiment, the cellular model is primary cells from mouse or human models. In yet another embodiment, the cellular model is stem cell or induced-pluripotent stem cell (iPSC). In an exemplary embodiment, the cellular model is an iPSC from a human patient or iPSC-derived cellular model of human diseases selected from a group consisting of cardiac diseases, alzheimer's disease (AD), other neurodegenerative diseases and fibrotic diseases.

The present disclosure primarily relates to synthesis of highly sensitive, red-emitting, fluorogenic dyes of compound of Formula I for applications including but not limiting to micro-viscosity and mitochondrial imaging.

Figure 1F:
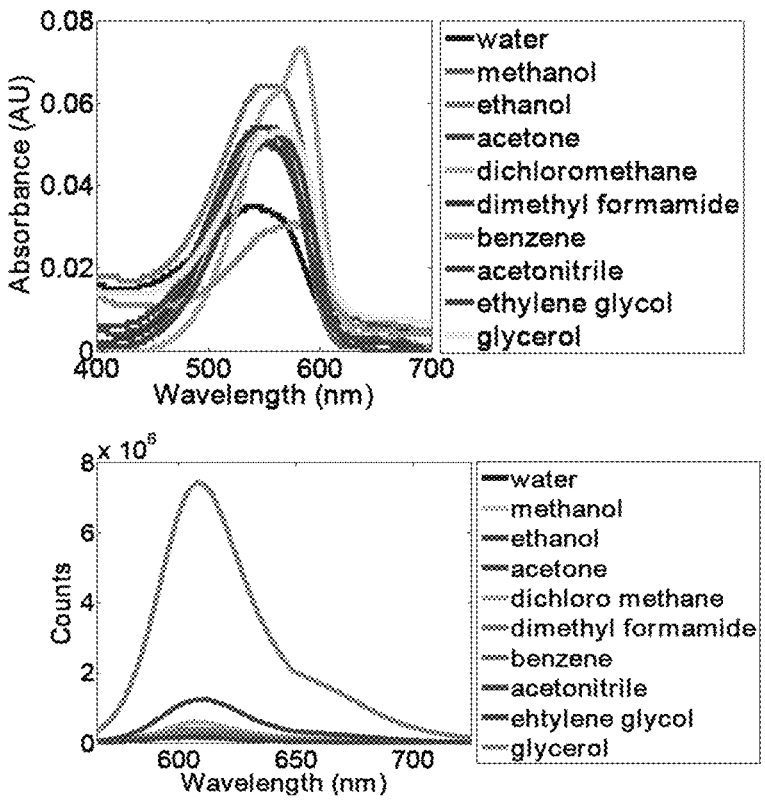
FIG. 1F: Absorption (upper panel) and fluorescence emission (lower panel) spectrum of 1 µM HC-1 in different solvents (specified in the inset).

In an embodiment of the present disclosure, the effect of viscosity of Formula I compounds was tested. The fluorescence of Formula I compounds HC-1 and HC-2 was measured in both water and glycerol. Both HC-1 and HC-2 dyes showed dramatically enhanced emission in glycerol versus water, with HC-1 (~70 fold) showing significantly greater increase as compared to HC-2 (~7 fold) (FIG. 1A-1C). HC-1 absorption and fluorescence were recorded in ten solvents of varying polarity and viscosity (FIG. 1F and Table 1 recited below). Studies demonstrated that HC-1 fluorescence quantum yield appears to correlate with solvent viscosity rather than polarity. To test the specificity of this HC-1 response, the effect of pH, metal ions and serum proteins were examined. pH has little or no effect on HC-1 emission over a broad pH range, with small changes in highly acidic (~pH 3) or basic pH (~pH 9) (FIG. 1D). Metal ions, serum proteins, plasmid DNA and reducing agent like glutathione (GSH) also did not significantly affect HC-1 emission (FIG. 1E).

Figures 2A, 2B, 2C, 2D:
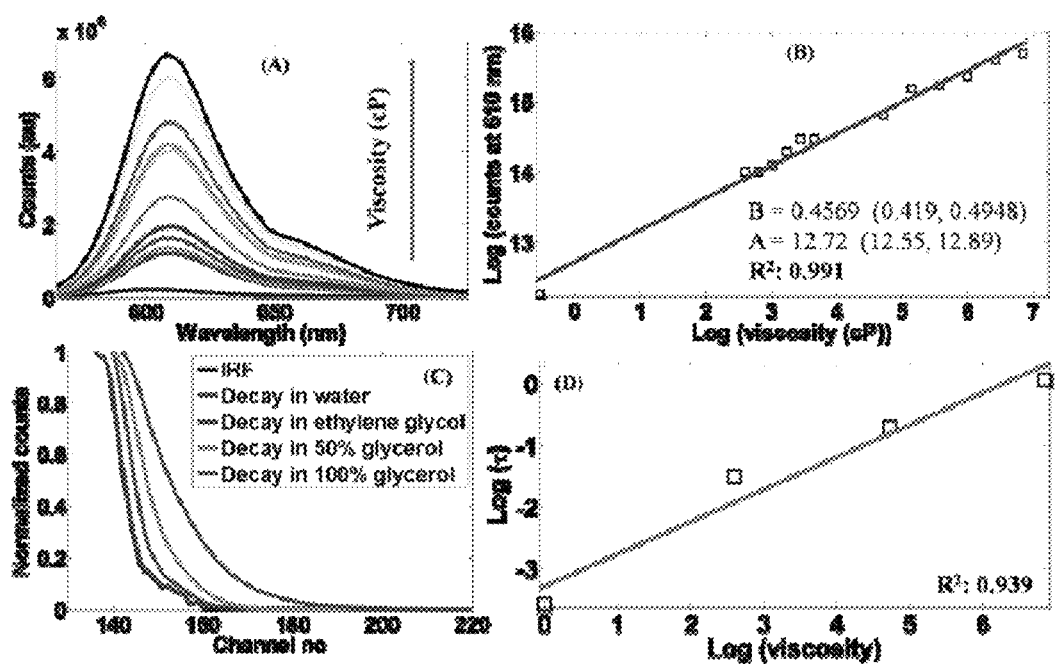
FIGS. 2A to 2D: Steady state and time resolved fluorescence of HC-1 is sensitive to viscosity. (A) Fluorescence spectra of HC-1 (2.5 mM) in ethylene glycol-glycerol mixtures of varying viscosity. (B) Log-log plot of fluorescence intensity versus viscosity in ethylene glycol-glycerol mixtures (open squares). Intensity data was fitted with Forster-Hoffmann equation (solid line). (C) HC-1 time resolved fluorescence decay profiles (solid lines) in ethylene glycol-glycerol mixtures, fitted as single exponential decay. (D) Log-log plot of fluorescence lifetimes with measured viscosities. Fitting of data with Forster-Hoffmann equation is also shown (solid line). R2 value is shown in the inset.

In another embodiment of the present disclosure, Systematic studies were carried out to understand the effect of viscosity on HC-1 fluorescence using ethylene glycol-glycerol binary solvent mixtures of different viscosity (13.5-950 cP) but of comparable polarity. FIG. 2A shows that the steady state fluorescence emission of HC-1 increases with increase in viscosity, with a max ~70 fold increase in 100% glycerol compared to in water (also see FIG. 2E). Importantly, time resolved fluorescence (TRF) measurements also confirmed HC-1 sensitivity to viscosity (FIG. 2C). In ethylene glycol-glycerol binary mixtures, HC-1 TRF profiles could all be fit as single exponential decays (FIG. 3D) and fluorescence lifetime values directly correlate with solvent viscosity (FIG. 2C). Log-log plot of fluorescence intensity and lifetime ($\tau$) versus viscosity ($\eta$) showed a linear relationship (FIGS. 2B and D). In all, solvent data showed HC-1 directly senses solvent viscosity, responding through increases in quantum yield and fluorescence lifetimes. For molecular rotors, the relationship between fluorescence and viscosity is described by the Förster-Hoffmann equation where 'I' is steady-state fluorescence intensity, $\tau$ is fluorescence lifetime and $\eta$ is the viscosity of the medium—

$$\log(I \text{ or } \tau) = A + B^* \log(\eta)$$

HC-1 viscosity sensing can be adequately described by the Förster-Hoffmann equation. Plots showing the effect of viscosity on fluorescence intensity (R2~0.991) as well as lifetime (R2~0.939) reveal a linear relationship and show a very good correlation with the Forster-Hoffmann equation (FIGS. 2B and D). Therefore, HC-1 functions as molecular rotor that is responsive to viscosity. According to Forster-Hoffmann theory, the slope B relates to the nature of the molecular rotor with a B value ~0.6 for a perfect rotor. Fitting of the present experimental data revealed a B value of ~0.46 for HC-1 (FIG. 2B). This value is higher than previously reported B values for other dyes, and indicates that HC-1 is a very sensitive probe for viscosity.

In yet another embodiment, Time Dependent Density Functional Theoretical (TD-DFT) calculations for HC-1 and HC-2 were performed to understand the effect of viscosity on the fluorescence quantum yield. TD-DFT calculations (Gaussian 09 package; Example 10) offered mechanistic insight into this viscosity sensing. Calculations showed that for HC-1, the oscillator strength for emission is significantly higher in ethylene glycol compared to water (Tables 3). This was consistent with increase in quantum yield for HC-1 with increasing viscosity. For some rotor-dyes, increasing viscosity is thought to inhibit the formation of a minimally fluorescent twisted internal charge transfer (TICT) excited state. Therefore, the inhibition of TICT formation in viscous media causes fluorescent enhancement. However, such a mechanism is applicable in cases where there is a strong propensity to form a viscosity sensitive, less fluorescent CT state.

Further, for HC-1, the TD-DFT calculations yield little evidence of charge transfer in the excited state. However, previous studies on merocyanine dyes, like HC-1, have shown loss of fluorescence through a distinct source of non-radiative decay—photoisomerization. This could be the reason for the ability of HC-1 to sense viscosity in the absence of a CT based mechanism. In fact, some previous studies report that the primary non-radiative route in such compounds is photo-isomerization. The DFT calculations in the present disclosure appear to support this model.

Figures 3A, 3B, 3C:
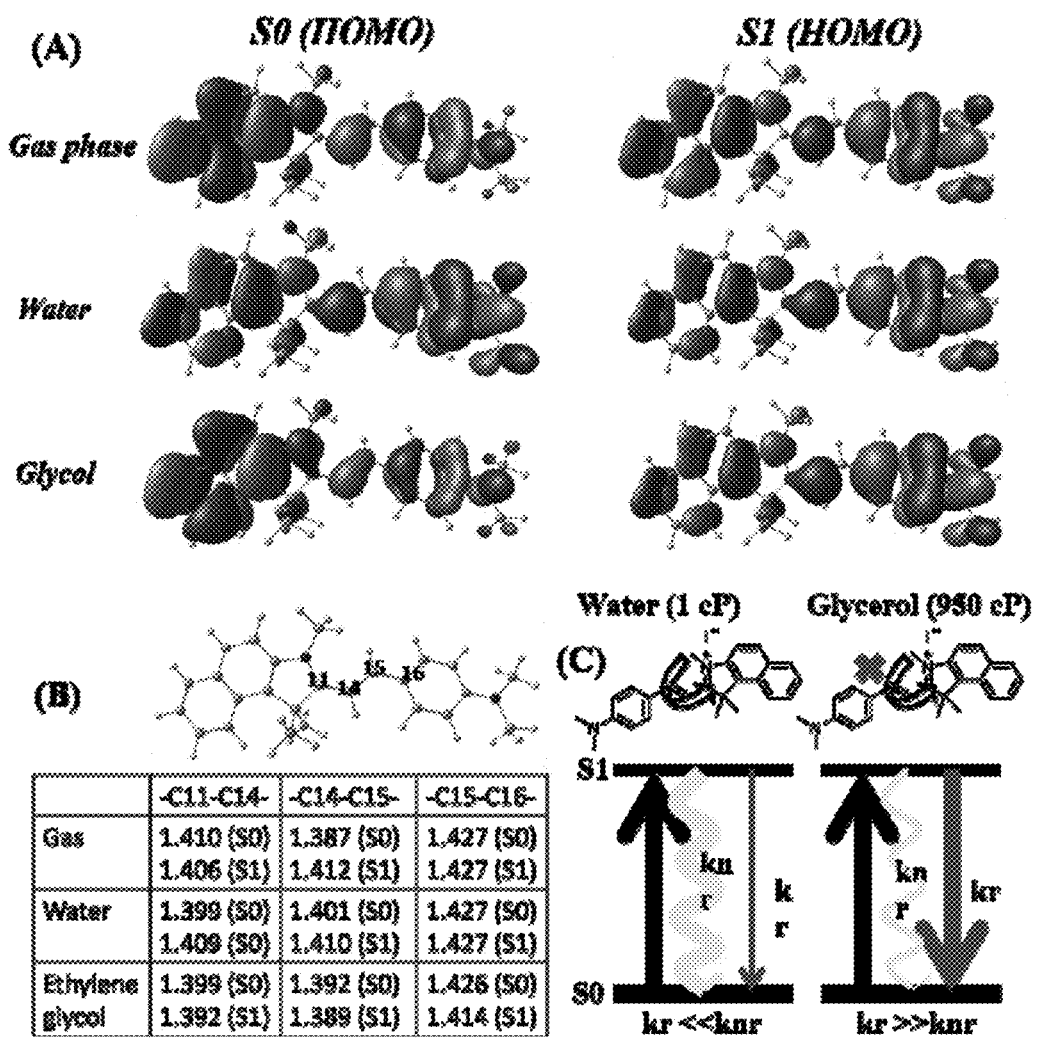
FIGS. 3A to 3C: Molecular orbital diagrams and bond lengths in different environments offer insight into mechanism of HC-1 viscosity sensing. (A) Frontier lobe diagrams at ground (S0) and excited state (S1) HOMO of HC-1 in gas phase, water and glycol medium. (B) Bond lengths of the central bonds are given in tabular form and (C) shows schematic representation of the proposed mechanism.

In still another embodiment, to examine the effect of viscosity on the nature of the excited state, the bond lengths of the central methine linker were examined. This was done with the expectation that a modulation of the rate of photo-isomerization would be reflected in a change in the excited state bond lengths of the central linker. It is clear from FIG. 3 that the bond lengths of all the central bonds (—C11-C14-, —C14-C15- and —C15-C16-) of HC-1 either increase or show little change upon photoexcitation in gas phase as well as in water. On the other hand, the length of these bonds in the excited state decreases in ethylene glycol (bond lengths are provided in tabular form in FIG. 3B). Especially noteworthy is the significant decrease observed in the excited state with the central bond (C14-C15) in ethylene glycol, completely opposite to what was seen in water and in the gas phase. Similarly, the frontier lobe molecular orbital diagrams of the excited state show that the bonding character of the central bonds significantly increases in glycol. Thus, the present disclosure shows that increased viscosity likely reduces non-radiative decay by attenuating the rate of photoisomerization, causing a concomitant increase in quantum yield. Here, the comparison with Formula I compound such as HC-2 is instructive. Since HC-2 has an extra vinyl bond it has a greater propensity for rotation that results in lower quantum yield as well as less sensitivity towards viscosity of the medium. The schematic representation of the presently proposed mechanism is shown in FIG. 3C.

Figures 4A, 4B:
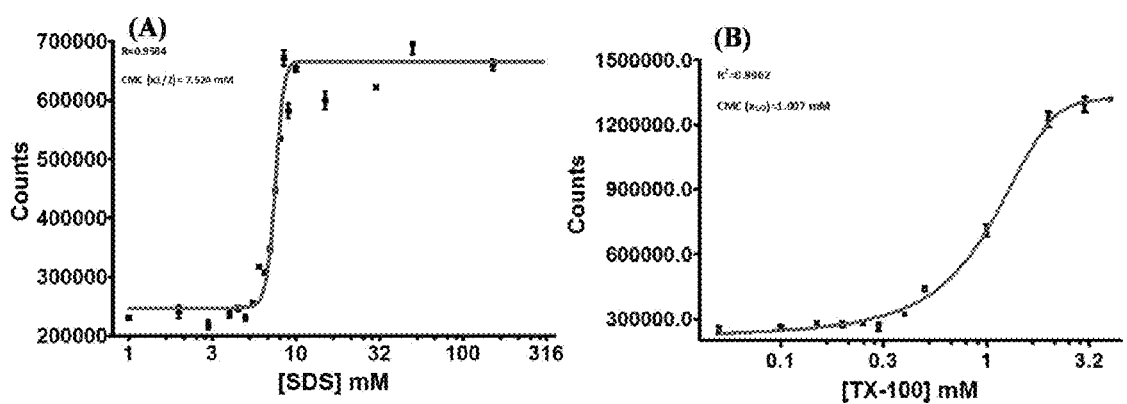
FIGS. 4A to 4B: HC-1 fluorescence is sensitive to viscosity and local ordering in surfactant micellar assemblies. Data showing changes in HC-1 fluorescence with increasing concentration of surfactants; sodium dodecyl sulphate (SDS) (A) and TritonX-100 (TX-100) (B); plotted on the log scale. Solid lines are the fitted curves obtained through sigmoidal fitting, which was then used to calculate the critical micellar concentration values, CMC (insets). Measured CMC values of ~7.5 and ~1 mM for SDS and TritonX-100 respectively, are comparable to values measured by standard methods.

In still another embodiment, further investigations were carried out to understand if Formula I compounds such as HC-1 can be used to probe the change in micro-viscosity associated with self-assembly of surfactants into micellar aggregates. FIG. 4 shows the change in fluorescence intensity with increasing concentration of Sodium Dodecyl Sulfate (SDS) (FIG. 4A) and TritonX-100 (FIG. 4B). Data shows a clear point of inflexion with an increase in fluorescence intensity corresponding to micelle formation. Fitting of the fluorescence intensity versus concentration plots yielded critical micellar concentration (CMC) values of ~7.5 and ~1 mM for SDS and TritonX-100 (TX-100) respectively. These measured CMC values are comparable to reported values and shows that Formula I compounds such as HC-1 is sensitive to aggregate formation. The data also reveals interesting new information about the local viscosity within the micelles. HC-1 reported a significantly larger increase in micro-viscosity associated with micelle formation for TritonX-100 (~7-fold fluorescence enhancement) as compared to SDS (~3-fold). Thus, Formula I compounds such as HC-1 are valuable probes for interrogating micro-viscosity in micro-heterogeneous media in new ways. Accordingly, the present disclosure describes interesting findings of micelle formation studies through a fluorescence micro-viscosity probe. This proposal is significant since micelles are a highly dynamic aggregates and Formula I compounds including HC-1 can report on micro-viscosity changes in these aggregates due to its high sensitivity.

Figures 5A, 5B, 5C, 5D, 5E, 5F:
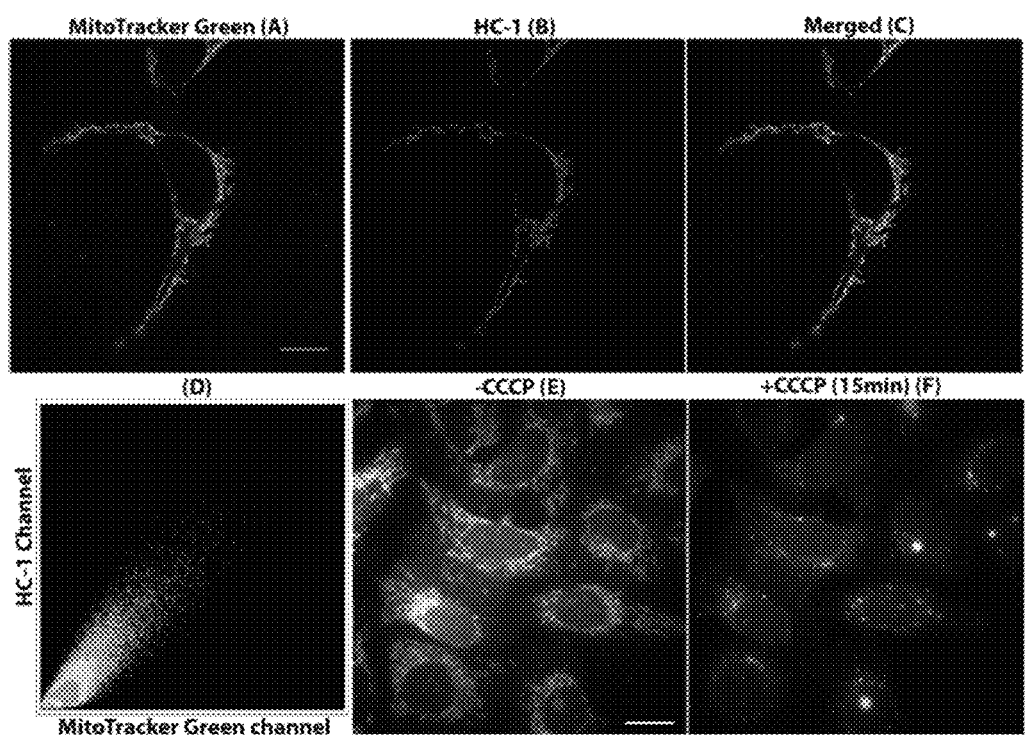
FIGS. 5A to 5F: HC-1 stains the mitochondria in live cells in a mitochondrial potential sensitive manner. Confocal fluorescence micrograph of live Human Bone Osteosarcoma Epithelial (U2OS) cells labelled with both MitoTracker Green (A) and HC-1 (B). Merged image (C) as well as 2D intensity correlation (Pearson R: 0.95) dot plot (D) indicate colocalization of the dyes. Scale bar: 20 micron. (E and F) Effect of Carbonyl Cyanide 3-Chloro Phenylhydrazone (CCCP) on HC-1 fluorescence in U2OS cells. Images acquired before (E) and after (F) addition of 5 µM (final concentration) CCCP. CCCP causes loss of HC-1 fluorescence showing it is sensitive to mitochondrial membrane potential. Scale bar: 20 micron.

In still another embodiment, additional studies were carried out to examine the suitability of Formula I compounds such as HC-1 as a probe for cellular micro-viscosity and intracellular staining, especially local changes in mitochondria. Confocal fluorescence micrographs of HC-1 treated human bone osteosarcoma epithelial cells (U2OS) cells confirmed that HC-1 is indeed cell permeable and stains live cells. Sub-cellular colocalization experiments performed with a standard mitochondrial probe (MitoTracker Green) and HC-1 confirmed that HC-1 indeed localizes to the mitochondria. FIG. 5(A-D) shows clear overlap in the merge image as well good correlation (R2: 0.95) in 2D intensity plot. Also, the present studies show that perturbation of the mitochondrial membrane potential (MMP) in cells by Carbonyl Cyanide 3-Chloro Phenylhydrazone (CCCP) treatment leads to a rapid and complete loss of HC-1 fluorescence (FIGS. 5E and F). These data show that Formula I compounds such as HC-1 stain mitochondria in live cells and are sensitive to MMP.

Figures 6A, 6B, 6C, 6D, 6E:
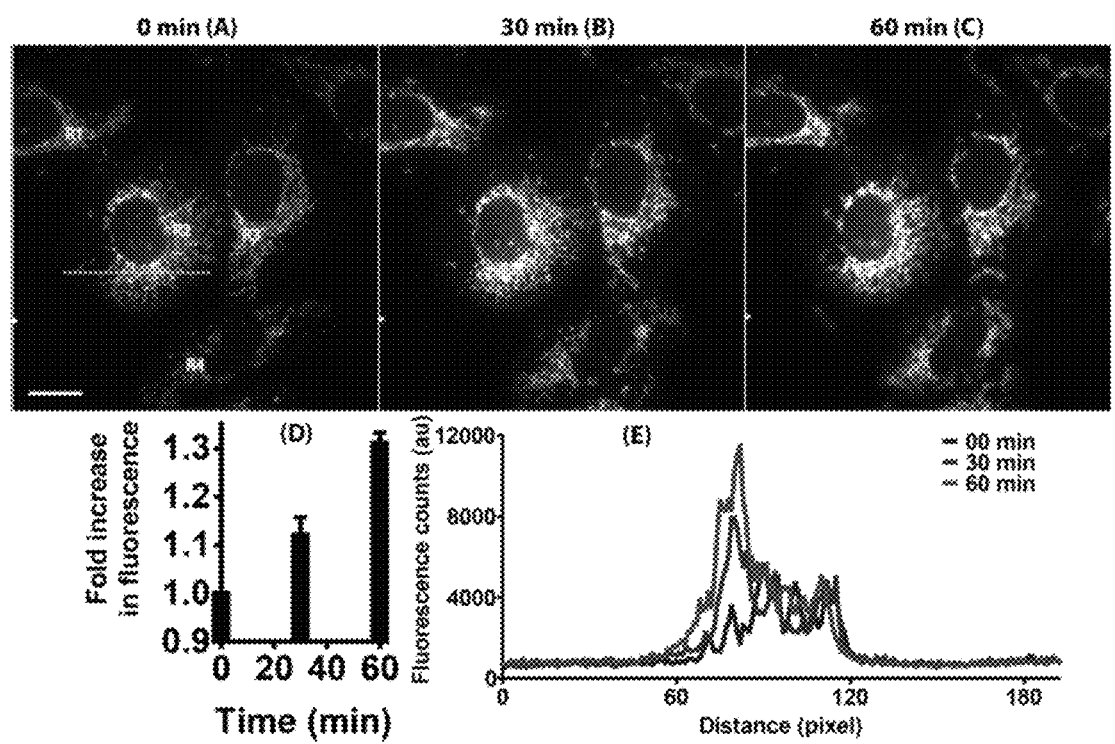
FIGS. 6A to 6E: HC-1 is sensitive to changes in local order and viscosity of mitochondria. Gray scale images show the effect of Monensin on HC-1 fluorescence in mitochondria. Confocal images were acquired just after addition (0 mins); after 30 and 60 minutes of 10 mM Monensin. Images are shown in gray scale. Quantitation of Monensin induced increase in fluorescence in specific regions of interest (ROIs) is shown in D (n=4). The four regions of interest (ROIs) chosen for analysis are marked in yellow (R1, R2, R3 and R4). Also, shown (E) is a line-scan analysis of fluorescence intensity change on the addition of Monensin. The line across the cell used for quantitation is marked on the image in panel A. Scale bar: 20 µM.

In still another embodiment, studies were performed to analyse whether Formula I compounds such as HC-1 fluorescence are sensitive to local mitochondrial viscosity, by treating HC-1 stained live cells with the polyether antibiotic Monensin. Monensin creates an ionic imbalance that results in matrix condensation and a resultant increase in mitochondrial ordering. Confocal fluorescence microscopy images showed that addition of Monensin (10 mM) caused a significant increase in HC-1 fluorescence (FIG. 6). Image quantitation of the live cell fluorescence (both selected regions of interest as well as a representative line scan analysis) confirms this finding (FIG. 6D). Overall, the studies in the present disclosure suggests that Formula I compound such as HC-1 is highly sensitive to changes in mitochondrial microenvironment. In particular, HC-1 can efficiently report on the Monensin induced increase in mitochondrial order through a clear increase in fluorescence.

In an exemplary embodiment of the present disclosure, Formula I compounds such as HC-1 are also capable of staining early mitochondria in live primary cells such as stem cells, including embryonic stem cells (ESCs). FIG. 7 shows fluorescence micrographs of HC-1 stained mouse ESCs as well as partly differentiated cells generated through the withdrawal of pluripotency factor, Leukemia Inhibiting Factor (LIF). HC-1 stained ESCs show bright staining of the mitochondrial structures, revealing a contiguous perinuclear mitochondrial ring like network as well some novel isolated spherical structures. These isolated mitochondrial puncta is a significant new finding, important in maintaining the overall mitochondrial function and organization. Overall, the mitochondrial staining by Formula I compounds such as HC-1 in ESCs is indeed striking/surprising finding. Particularly, HC-1 revealed that the perinuclear ring like network may be a key feature of mitochondria in stem cells. Even partly committed cells immediately lose this feature, showing a more reticulated, spread-out network. Interestingly, early-differentiated cells that show cellular protrusions and membrane processes show significant mitochondrial densities in these sub-cellular structures. The data of the present disclosure has shed new light on mitochondrial network in stem cells as well as cells in early differentiation and suggest that Formula I compounds such as HC-1 are powerful, broadly applicable and sensitive probes for studying mitochondrial organization and dynamics. The present disclosure also demonstrates that Formula I compounds including HC-1 have low toxicity and is suitable for long term imaging of live stem cells (FIG. 8).

In yet another exemplary embodiment, Formula I compounds such as HC-1 can be used to study and image the changes in the cell state and function, and for screening cellular models of human disease. As Formula I compounds such as HC-1 are sensitive to the local order or the viscosity of the mitochondria, this can be used to estimate change in local order of the mitochondria during changes in cell state and function.

Figure 14:
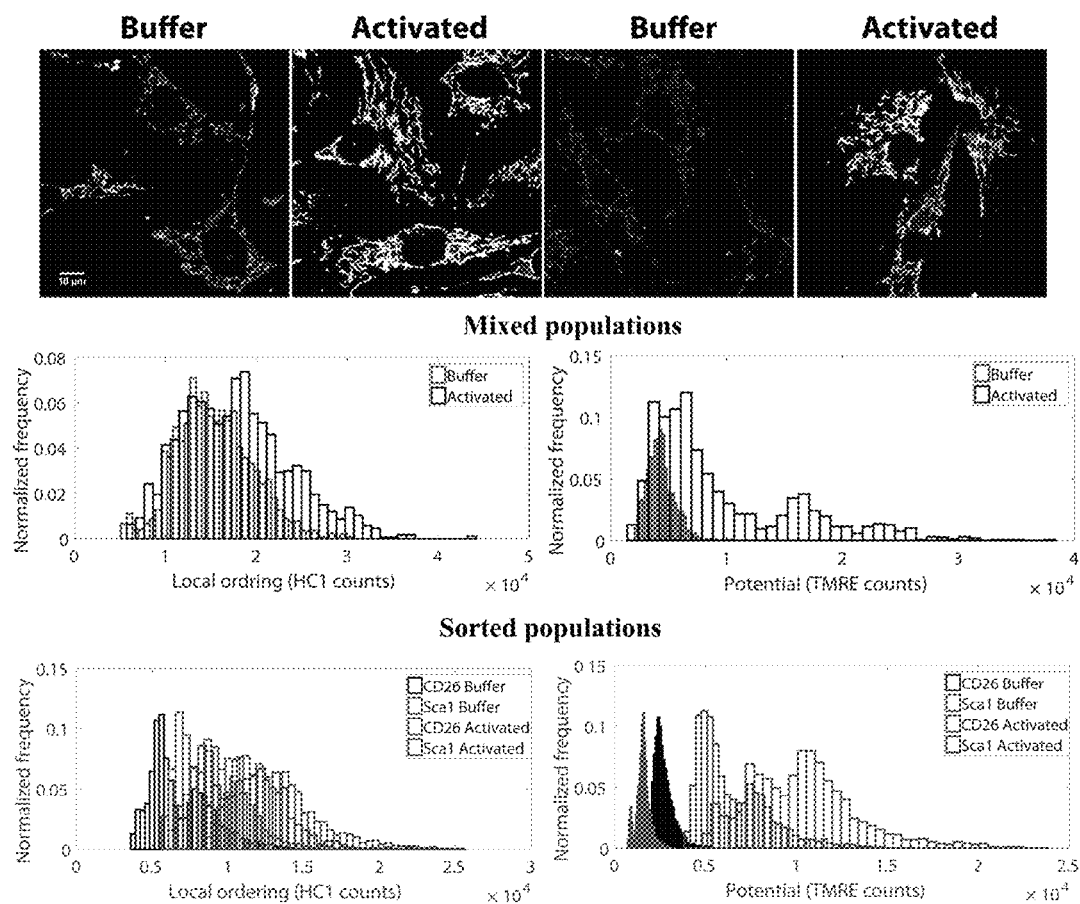
FIG. 14: HC-1 is sensitive to local order and viscosity of mitochondria allowing new measurement of cell state and function. Measurement of mitochondrial local ordering allows imaging of mitochondrial heterogeneity and changes in mitochondrial state and function. Said new measurements of mitochondria and cell function are made possible through multi-parametric imaging. Local order and viscosity of mitochondria during fibroblast activation can be probed by imaging HC-1 stained mitochondria while changes in mitochondrial potential can be imaged through changes in fluorescence of HC-1 and TMRE.

Specifically, in an exemplary embodiment, HC-1 can be used to estimate changes in local ordering of the mitochondria of primary cells such as primary fibroblasts. In experiments with primary fibroblasts, on receiving stimuli fibroblasts are known to get activated and mimic properties of fibroblasts in the fibrotic condition. Specifically, these activated fibroblasts showed increased migration and formation of myofibroblasts that are capable of contracting the extracellular matrix. Mitochondrial imaging using Formula I compounds such as HC-1 showed an increase in local ordering of the mitochondria (along with increase in mitochondrial potential imaged through TMRE) (FIG. 14) in activated fibroblasts. Furthermore, HC-1 imaging is efficacious in imaging the differences in the local ordering of the mitochondria, even within the same set of cells. Also, mitochondrial imaging through HC-1 shows large changes in the local ordering of ONLY in a sub-set of the activated fibroblast (CD26 cells). Interestingly, the increase in mitochondrial local ordering is much more only for a sub-set of cells, despite all cells getting the same apparent stimulus (FIG. 14, lower panel). This observed increase in HC-1 fluorescence sensitive to local ordering is significantly higher for the CD26 primary fibroblasts, that have contractile properties than for Sca 1 positive cells resembling activated fibroblast cells that showed increased migration. In this embodiment, HC-1 imaging was used to measure changes in cell state and function using imaging of mitochondrial local ordering, viscosity and function.

Thus, the present disclosure provides unique fluorescence based imaging probes/dyes (Formula I compounds) that can report on intracellular heterogeneity and local microenvironments in living cells which is extremely valuable. Also, the present disclosure describes an easy and one step synthesis of said Formula I compounds. The Formula I compounds, especially HC-1 are red-emitting ($\lambda_{max}$-610 nm) probes for micro-viscosity, mitochondrial staining and local order in living cells including live primary cells such as stem cells/embryonic stem cells (ESCs). These sensitive and versatile dyes respond through changes in intensity and lifetime, and are sensitive enough to report on micro-viscosity changes associated with highly dynamic surfactant micelles. Interestingly, TD-DFT calculations showed that the specific Formula I compound HC-1 may sense viscosity through a novel, photoisomerization-based mechanism. While the fluorescence intensity and lifetime data from HC-1 can be described in terms of the Förster-Hoffmann equation used for molecular rotors, the mechanism of the HC-1 'rotor' action appears to be different from known TICT 'rotor' dyes. Further Formula I compounds such as HC-1 is a sensitive stains for mitochondria in living cells, and can respond to changes in mitochondrial order. Further, the present disclosure demonstrates that the Formula I compound HC-1 can also stain the nascent mitochondrial network in embryonic stem cells and reveal novel mitochondrial staining patterns. HC-1 reveals perinuclear mitochondria in ESCs with additional localized mitochondrial puncta. HC-1 also helps visualize significant mitochondrial remodelling seen even in early differentiation, with reticulated mitochondrial enrichment in cell protrusions and processes. These results indicate that environmentally sensitive fluorescent dyes may offer new ways of imaging cellular transitions. Thus, compound of Formula I (such as HC-1 and HC-2) are easy to synthesize, unique fluorescent probes for micro-viscosity and mitochondrial imaging in stem cells and cell fate switching.

Additional embodiments and features of the present disclosure will be apparent to one of ordinary skill in art based upon description provided herein. The embodiments herein and the various features and advantageous details thereof are explained with reference to the non-limiting embodiments in the description. Descriptions of well-known/conventional methods and techniques are omitted so as to not unnecessarily obscure the embodiments herein. The examples presented herein are intended merely to facilitate an understanding of ways in which the embodiments herein may be practiced and to further enable those of skill in the art to practice the embodiments herein. Accordingly, the following examples should not be construed as limiting the scope of the present disclosure.

EXAMPLES

Materials

Chemicals: All the chemicals are purchased from Sigma-Aldrich unless otherwise specified in the respective section.
Cell-lines: human osteosarcoma cells (U2OS), human embryonic kidney cells (HEK), mouse and human primary fibroblasts, mouse embryonic stem cells (mESC) and human pluripotent stem cells (PSC). U2OS and HEK 293 cell lines were procured from ATCC, USA. The primary mouse and human fibroblasts were kind gifts from Dr. Colin Jamora, inStem and Dr. Shravanti Rampalli, inStem respectively. The mouse and human pluripotent cells were kind gifts from Dr. Tina Mukherjee, inStem and Dr. Ravi Muddashetty, inStem respectively.
Data analysis: Matlab, R2009a (MATHWORKS, USA), ImageJ and Graphpad Prism (version 5) were used to analyse all the data.

Example 1

General Synthetic Procedure for Preparing Compound of Formula-I:

A mixture of compound of Formula-III (5.00 mmol), and substituted/unsubstituted aldehyde derivative (5.00 mmol) was added in presence of 10 ml anhydrous ethanol. 0.5 ml of piperidine was added to this mixture and the resultant reaction mixture was refluxed for about 2 to 4 hours followed by cooling to obtain the precipitate. The precipitated solid was filtered and then purified by column chromatography using DCM/Methanol and the eluent yielded compound of Formula I.

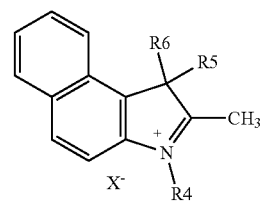

Formula III wherein
'R4', 'R5' and 'R6' are individually selected from a group consisting of hydrogen, alkoxy and alkyl; and
'X' is selected from a group consisting of I, Cl, Br and F.

Example 2

Synthesis of HC-1

(E)-2-(4-(Dimethylamino)styryl)-1,1,3-trimethyl-1H-benzo[e]indol-3-ium iodide (HC-1)

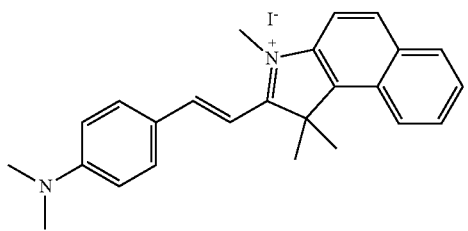

Figure 16:
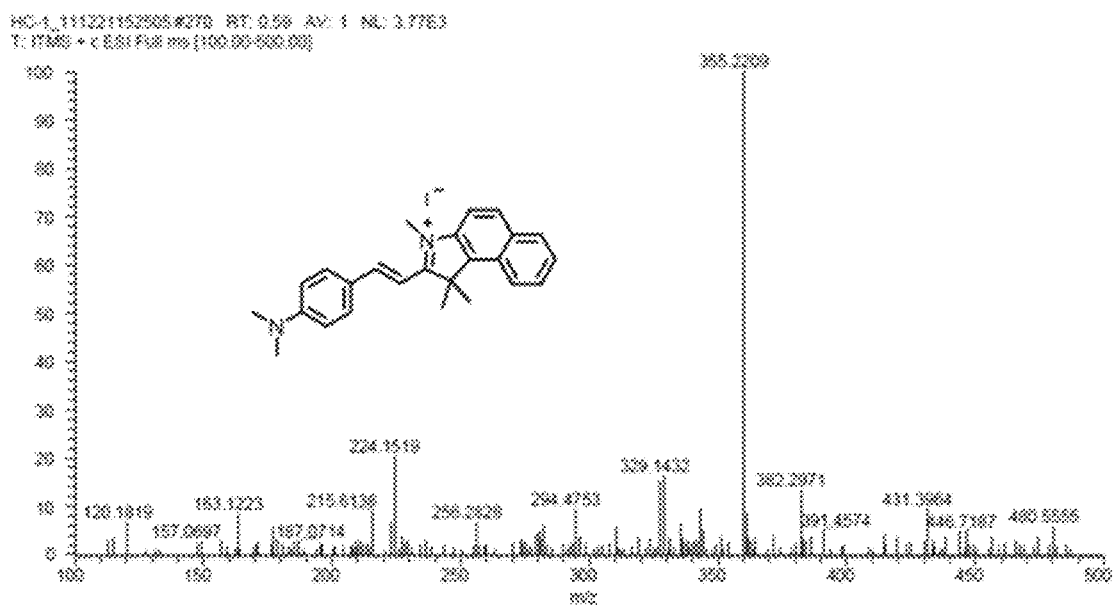
FIG. 16: Mass spectroscopic analysis of HC-1.
Figure 18:
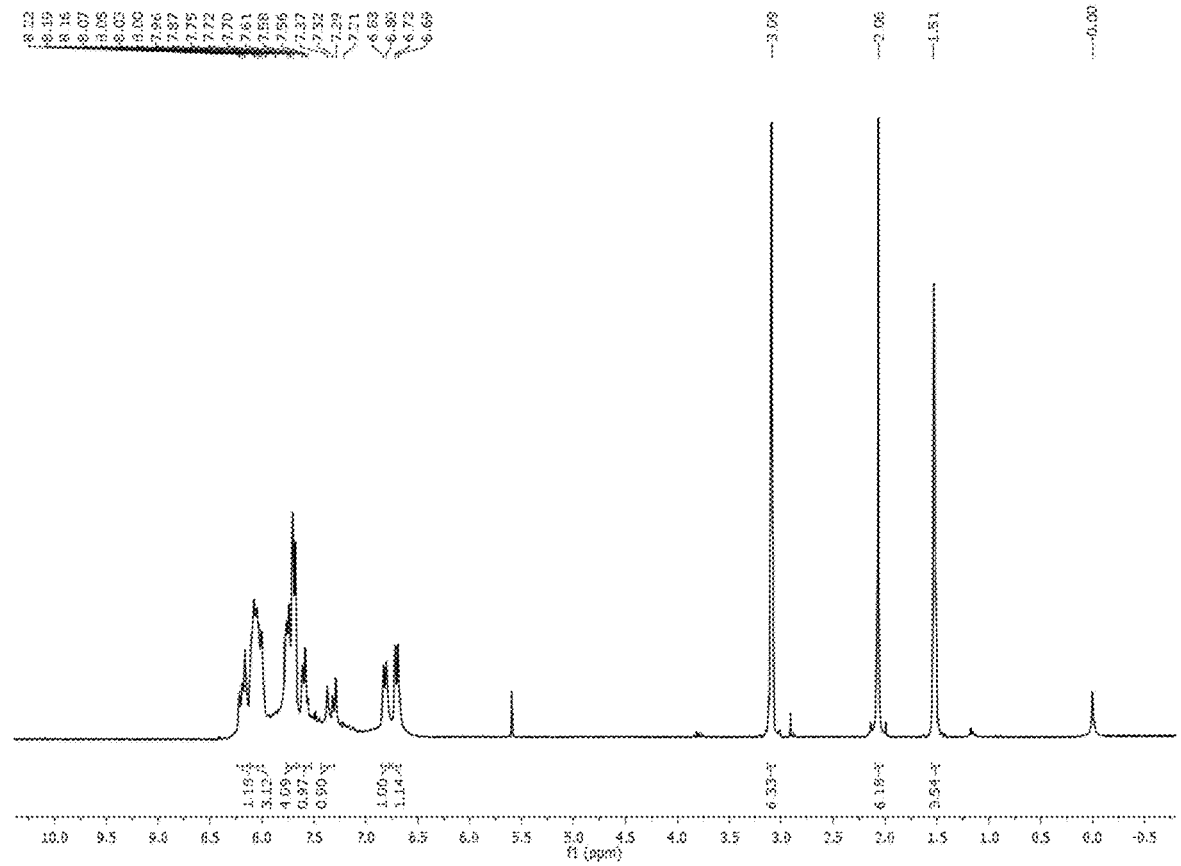
FIG. 18: Proton Nuclear Magnetic Resonance spectroscopic analysis of HC-1.
Figure 19:
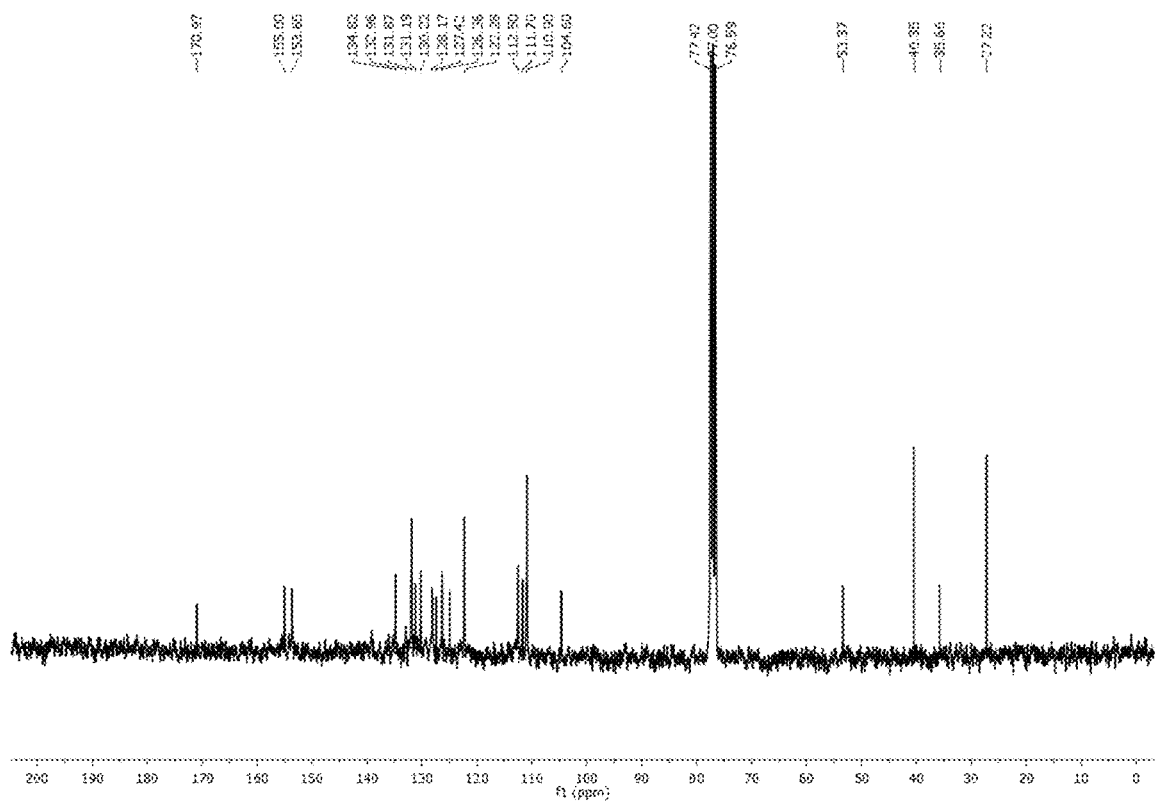
FIG. 19: $C^{13}$ Nuclear Magnetic Resonance spectroscopic analysis of HC-1.

A mixture of 1,1,2-trimethyl-1H-benzo[e]indolium iodide (5.00 mmol), 4-(dimethylamino)benzaldehyde (5.00 mmol) was added with 10 ml anhydride ethanol, and to this mixture 0.5 ml of piperidine was added and was refluxed for about 3 hours. After cooling to room temperature, the red solid was precipitated. The precipitated red solid was filtered and then purified by column chromatography using DCM/Methanol as the eluent yielded brick red solid HC-1. Mass Spectroscopy (MS), proton and $C^{13}$ nuclear magnetic resonance (NMR) spectroscopy of HC-1 are provided in FIGS. 16, 18 and 19, respectively.

Example 3

Synthesis of HC-2

2-((1E,3E)-4-(4-(Dimethylamino)phenyl)buta-1,3-dien-1-yl)-1,1,3-trimethyl-1H-benzo[e]indol-3-ium iodide

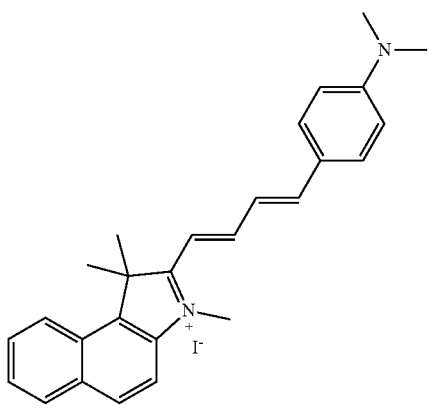

Figure 17:
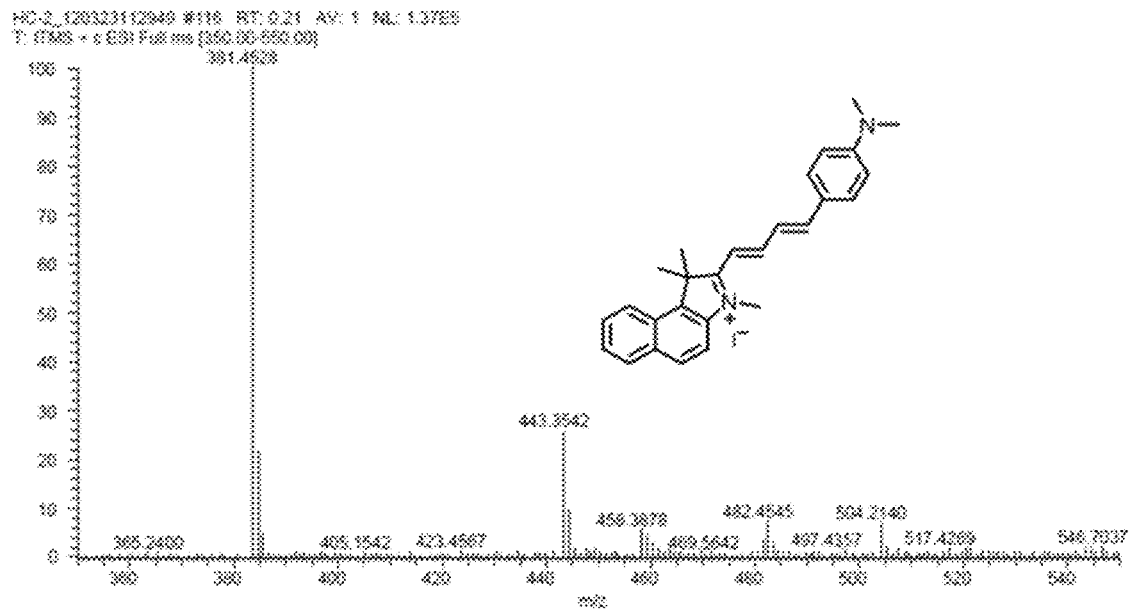
FIG. 17: Mass spectroscopic analysis of HC-2.
Figure 20:
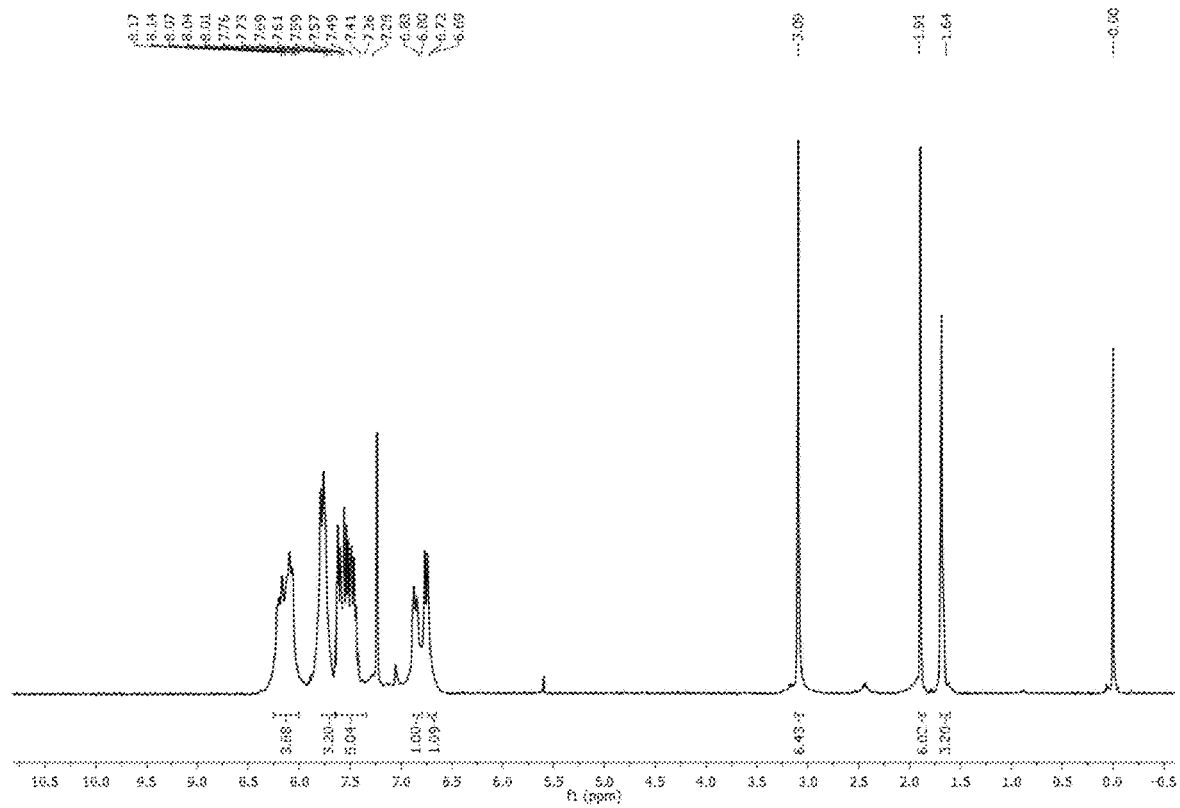
FIG. 20: Proton Nuclear Magnetic Resonance spectroscopic analysis of HC-2.
Figure 21:
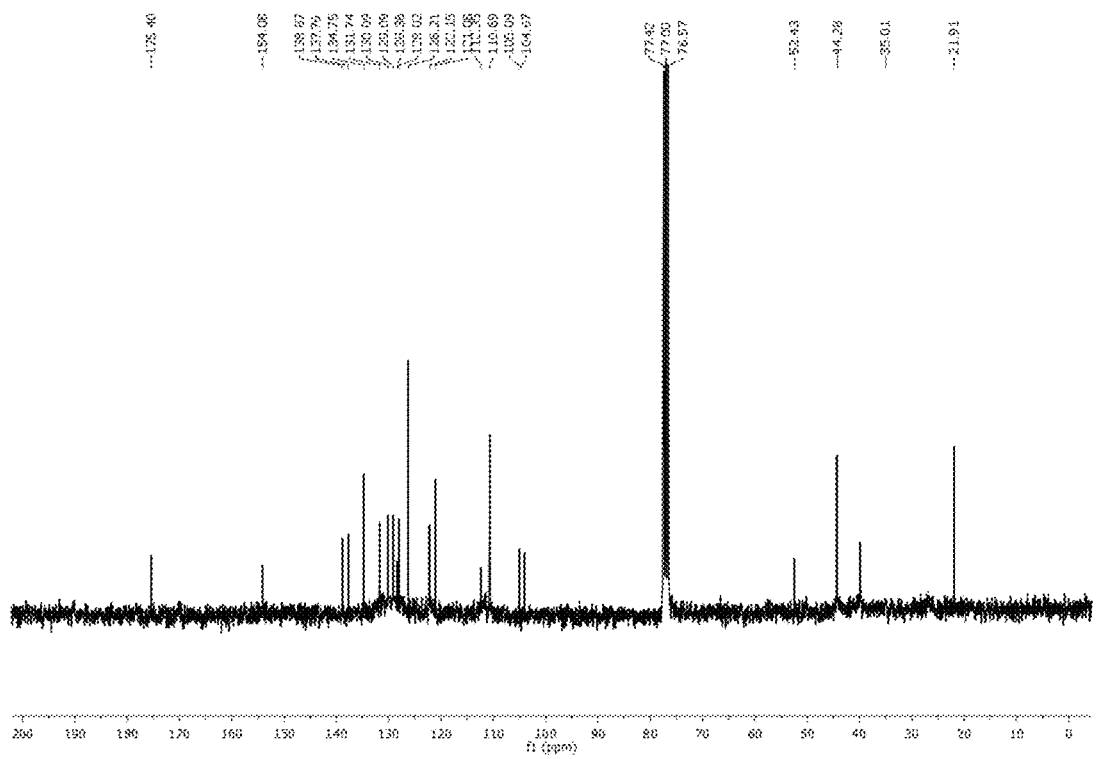
FIG. 21: $C^{13}$ Nuclear Magnetic Resonance spectroscopic analysis of HC-2.

A mixture of 1,1,2-trimethyl-1H-benzo[e]indolium iodide (5.00 mmol), 4-(dimethylamino)cinnamaldehyde (5.00 mmol) was added with 10 ml anhydride ethanol, and to this mixture 0.5 ml of piperidine was added and was refluxed for 3 hours. After cooling to room temperature, the dark blue solid was precipitated. The precipitated dark blue solid was filtered and then purified by column chromatography using DCM/Methanol as the eluent yielded dark blue solid HC-2. Mass Spectroscopy (MS), proton and $C^{13}$ nuclear magnetic resonance (NMR) spectroscopy of HC-2 are provided in FIGS. 17, 20 and 21, respectively.

Example 4

Staining and Imaging of Live Cells by Formula I Compounds:

Formula I compounds (dyes) are positively charged and can be easily targeted to the mitochondria of the live cells. The dyes are highly specific for functional mitochondria. Localization is confirmed by 'colocalization' assays with mitochondria specific commercial dyes and high-resolution microscopy. The protocol for making working solution and staining mitochondria of live cells for imaging is as follows:
  (i) 1.2 mg of solid Formula I compound HC-1, or 1.3 mg of solid Formula I compound HC-2 was taken in a dark colored container and dissolved in 1 ml of tissue culture grade 50% DMSO-water mixture to make a stock solution of 1 mM. This stock solution was stored at about 4° C. This stock solution is stable for one year and can be used for longer time (more than a year), but emission spectra should be compared with the initial one prior to use,
  (ii) 0.25-0.5 μL of stock solution was added in 2 ml of fresh and pre-warmed (37° C.) media which yielded the final concentration of the medium to 125-250 nM,
  (iii) Cells from the incubator were taken out and the old media was discarded are the cells were washed with 1× phosphate buffer saline (PBS),
  (iv) Dye-containing media was added to the washed cells and the cells were incubated in incubator for about 15-30 minutes to obtain stained cells,
  (v) The cells were then taken out from the incubator and washed twice by 1×PBS. Pre-warmed fresh media containing HEPES buffer was added to the stained cells, and
  (vi) Cell imaging was carried out using a fluorescence microscope—Excitation source: 543 nm or 561 nm for HC-1 and 561 nm or 640 nm for HC-2—Emission: 590 nm-675 nm for HC-1 and from 650 nm-750 nm for HC-2 (changed accordingly during multicolour imaging).

Figures 11A, 11B, 11C:
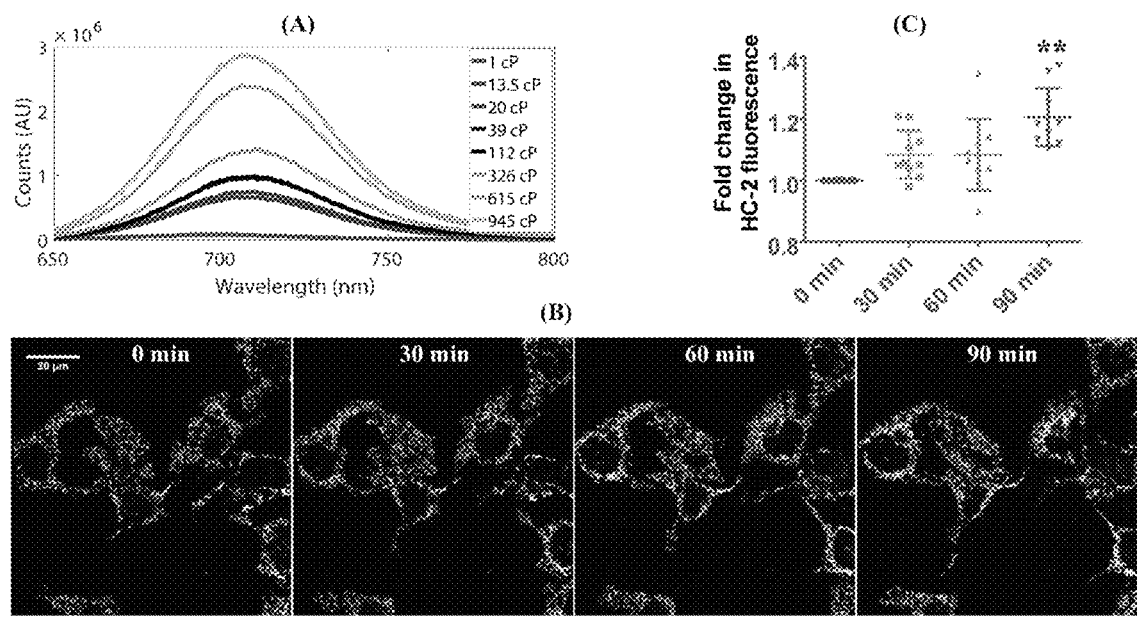
FIGS. 11A to 11C: (A) HC-2 fluorescence is sensitive to local order and viscosity. Effect of solvent viscosity on steady state fluorescence intensity of HC-2 (Excitation wavelength was 620 nm). Viscosity of the media was increased by adding increasing amount of glycerol in ethylene glycol-glycerol binary mixture. (B) Effect of Monensin (10 µM) on HC-2 stained (250 nM) mitochondria of live HEK 293 cells. Time dependent increase in fluorescence intensity after addition of Monensin indicates that HC-2 also like HC-1 is sensitive to Monensin induced alteration in local ordering of mitochondria within live cells. (C) Quantification and statistical analysis of the change in HC-2 fluorescence after addition of Monensin.
Figure 12:
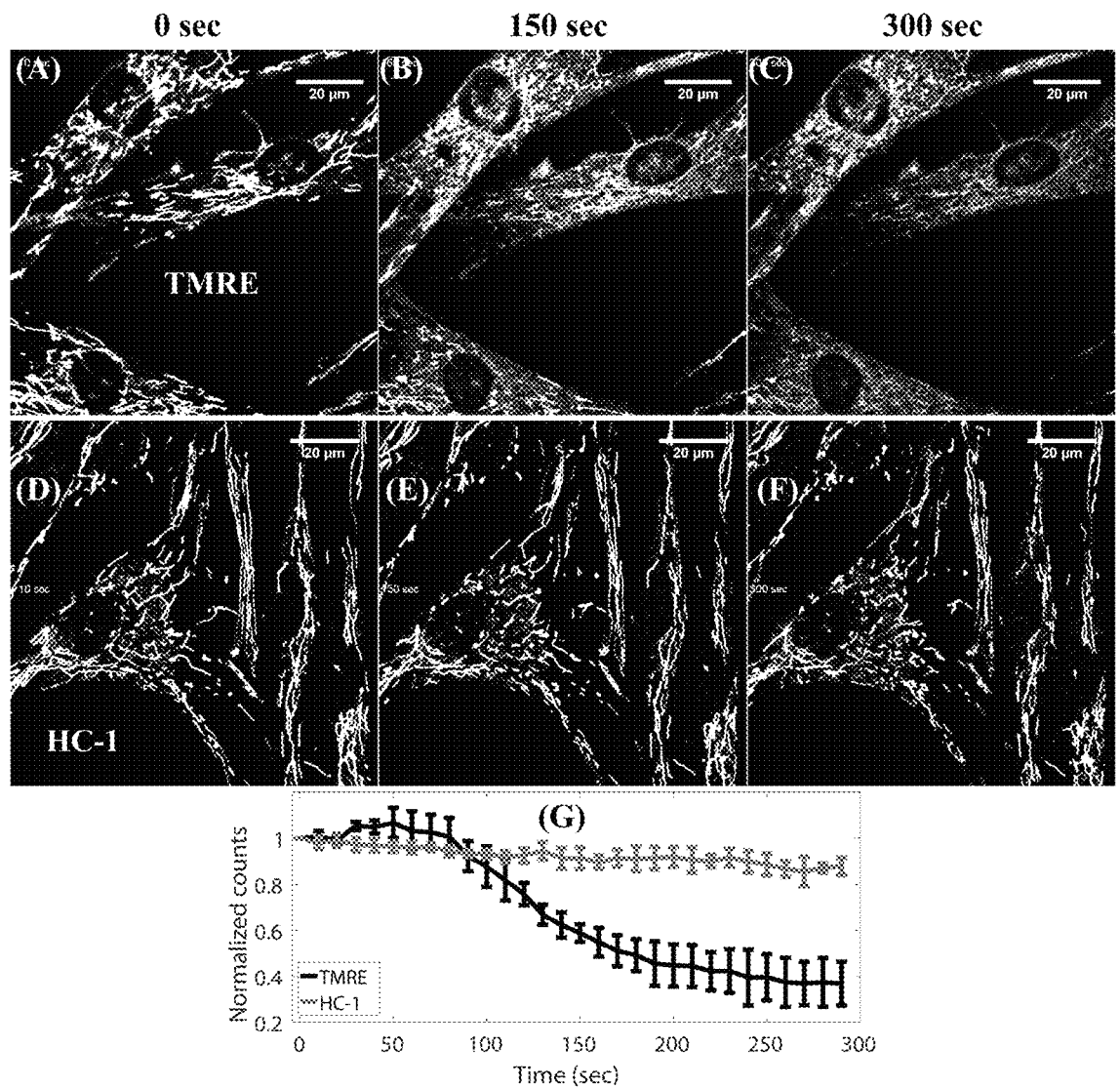
FIG. 12: HC-1 showed low photo-toxicity during repeat photo-illumination and fast mitochondrial imaging. This allows repeat photo-illumination with high temporal resolution and measurement of mitochondrial mobility and dynamics. Human primary fibroblasts were stained either with tetramethylrhodamine, ethyl ester (TMRE) (upper and middle panel) or with HC-1 (lower panel). Images of upper panel (A, B and C) and middle panel (D, E and F) acquired using 0.1% and 0.75% power of 561 nm laser, respectively. Disappearance of dye fluorescence from mitochondria and increase in cellular (background) fluorescence (compare A with B and C and compare D with E and F) clearly indicates that irradiation induced depolarization of mitochondrial membrane when cells are stained and imaged with TMRE, a commercial dye. However, such dramatic loss of fluorescence is not seen when HC-1 is used for staining and imaging mitochondria. Lower panel (G) shows the intensity-based quantification to show persistence of fluorescence at the mitochondria (site of staining) during imaging.

The results of this study are also provided in FIGS. 10A-10F (colocalization assay with HC-2 and effect of CCCP on HC-2 stained mitochondrial fluorescence) and FIGS. 11A-11C (sensitivity of HC-2 towards bulk and micro-viscosity). FIG. 12 (photo-stability/toxicity and stability of HC-1 or TMRE based mitochondrial staining in human primary fibroblast cells) further shows that the dyes HC-1 and HC-2 are suitable for long-term imaging and highly photo-stable and not phototoxic unlike commercially available probes like TMRE; and FIG. 13 (HC-1 and HC-2 staining in mitochondria of hPSCs) shows uniform staining of mitochondria by HC-1 and HC-2 in live hPSCs. FIG. 14 further shows that HC-1 imaging can be used to measure changes in local ordering and viscosity of mitochondria during primary mouse fibroblast activation. HC-1 imaging showed that local order and viscosity of mitochondria can be used to measure differential fibroblast activation in distinct cellular populations. Such cellular heterogeneity can be probed by multi-parametric imaging of the mitochondria using HC-1 and TMRE.

Example 5

UV-Vis and Steady State Fluorescence Study:

UV-Vis measurement was performed in Shimadzu UV-Vis spectrophotometer (U2600) and steady state fluorescence study was performed in Horiba-Yobin (Fluorolog3) fluorescence spectrophotometer. For all the fluorescence measurements, excitation and emission slits were kept constant at 2 nm (except studies on pH dependence: excitation/emission=2/4 nm respectively). Final concentration was 2.5 µM (except for measurement of fluorescence quantum yield [1 µM] and lifetime [25 µM]) for all the spectroscopic studies.

The HC-1 absorption and fluorescence were recorded in ten solvents of varying polarity and viscosity. The results are provided in FIG. 1F and Table 1.

TABLE 1

Photo-physical parameters of HC-1 in ten different solvents

| Solvents | Viscosity (cP) | Polarity (ET(30)) | $\lambda_{abs}$ (nm) | $\lambda_{em}$ (nm) | Quantum yield |
|---|---|---|---|---|---|
| Water | 1 | 63.1 | 542 | 605 | 0.034 ± 0.001 |
| Methanol | 0.6 | 33.6 | 552 | 603 | 0.018 ± 0.0002 |
| Ethanol | 1.2 | 51.9 | 556 | 607 | 0.024 ± 0.0002 |
| Acetone | 0.32 | 20.7 | 553 | 606 | 0.014 ± 0.0002 |
| DCM | 0.43 | 40.7 | 553, 583 | 608 | 0.033 ± 0.0005 |
| DMF | 0.85 | 43.2 | 553 | 610 | 0.028 ± 0.0003 |
| Acetonitrile | 0.37 | 45.6 | 577 | 613 | 0.028 ± 0.0002 |
| Benzene | 0.6 | 34.3 | 548 | 608 | 0.014 ± 0.0001 |
| Ethylene glycol | 13.5 | 56.3 | 562 | 610 | 0.087 ± 0.0004 |
| Glycerol | 9.50 | 56.9 | 564 | 610 | 0.477 ± 0.0005 |

Example 6

Effect of pH, Ions, Serum Protein, Plasmid DNA and Glutathione on HC-1 Fluorescence:

0.1 M buffers of identical ionic strength solution were used for carryout the experiments. For pH 3, 4, 5 and 5.5, acetate buffer was used, for pH 6.2, 6.9 and 7.4, phosphate buffer was used and for pH 8 and 9.2, Tris-HCl buffer was used. The used salts were Sodium Chloride (NaCl), Potassium Chloride (KCl), Magnesium Chloride ($MgCl_2$), Zinc Chloride ($ZnCl_2$), Nickel Chloride ($NiCl_2$) and Ferric Chloride ($FeCl_3$). Final concentration of the cations (except Zn) was 10 mM and prepared in 1× Phosphate Buffer Saline. For Zn (II), saturated aqueous solution was used. Bovine Serum Albumin (BSA), plasmid DNA and glutathione concentration were at 1 mg–ml$^{-1}$, 5 µg–ml$^{-1}$ and 10 µM respectively. In all cases, HC-1 concentration was 2.5 µM. Fluorescence measurement was performed after 30 minutes of incubation.

The results of the experiment are shown in FIGS. 1D and 1E. It was seen that pH has little or no effect on HC-1 emission over a broad pH range, with small changes in highly acidic (~pH 3) or basic pH (~pH 9) [FIG. 1D]. Metal ions, serum proteins, plasmid DNA and reducing agent like glutathione (GSH) also did not significantly affect HC-1 emission [FIG. 1E].

Example 7

Measurement of Fluorescence Quantum Yield of HC-1:

The absorbance values of the reference solution and HC-1 was ensured in different solvents were all ~0.06, in order to obtain a reliable measure of the quantum yield. An aqueous solution of Rhodamine B was used as reference. Fluorescence (integrated intensities) and absorbance values were obtained and the quantum yield was calculated using the following equation;

$$\varphi = \varphi_r \times \left( \frac{1 - 10^{-A_r L}}{1 - 10^{-A \cdot L}} \right) \times \frac{N}{N_r} \times \frac{\int I}{\int I_r}$$

$\varphi$ and $\varphi_r$: Quantum yield of sample and reference (0.55) respectively; A and $A_r$: Absorbance of sample and reference respectively; L: path length of the cuvette (here is same); N and $N_r$: refractive index of the solvents containing sample and reference; I and $I_r$: Integrated intensity of fluorescence emission of sample and reference respectively.

The study demonstrates that HC-1 fluorescence quantum yield appears to correlate with solvent viscosity rather than polarity.

Example 8

Effect of Solvent Viscosity on Fluorescence of HC-1 and HC-2:

To check the viscosity effect, Ethylene glycol-glycerol mixtures were used to prepare the solutions of varying viscosity to carry out the viscosity studies. Absolute value of the viscosity of the mixture was calculated using the following equation $$\log(\eta) = v1 * \log(\eta 1) + v2 * \log(\eta 2)$$

where η is the viscosity of the mixture, v1 and v2 are the volume fraction in the mixture and η1 (13.5 cP) and η2 (945 cP) are the viscosity of ethylene glycol and glycerol respectively. The prepared mixtures were sonicated for 5 minutes to remove the air bubbles prior to fluorescence measurements.

Figure 2E:
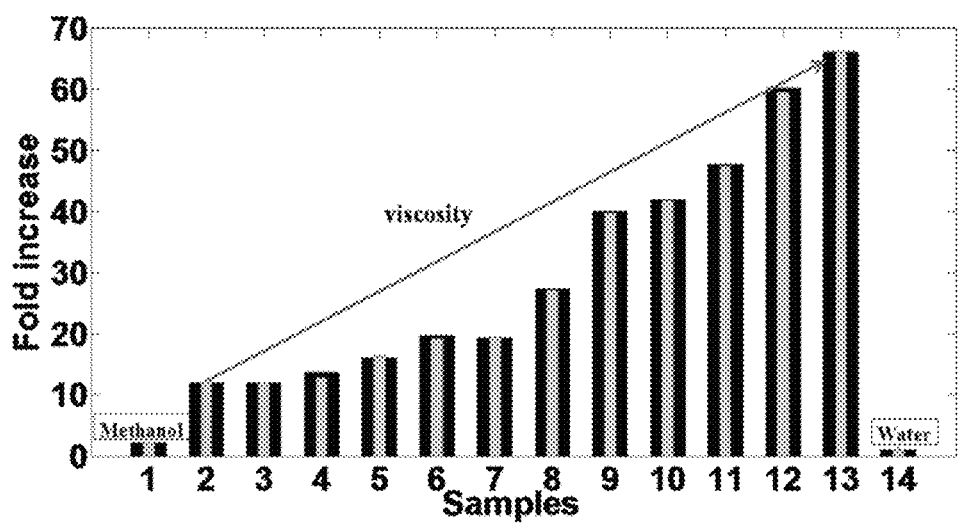
FIG. 2E: Fold increase of fluorescence intensity of HC-1 with increasing viscosity of the medium compared to intensity in water. Black and orange bars represent duplicate measurements. Sample 2 and 13 are ethylene glycol (13.5 cP) and glycerol (950 cP) respectively. Samples 3 to sample 12 are the binary mixture of ethylene glycol and glycerol with increasing viscosity.

FIG. 2A shows that the steady state fluorescence emission of HC-1 increases with increase in viscosity, with a max ~70 fold increase in 100% glycerol compared to in water (also see FIG. 2E). Importantly, time resolved fluorescence (TRF) measurements also confirmed HC-1 sensitivity to viscosity (FIG. 2C). In ethylene glycol-glycerol binary mixtures, HC-1 TRF profiles could all be fit as single exponential decays (FIG. 3D) and fluorescence lifetime values directly correlate with solvent viscosity (FIG. 2C). Log-log plot of fluorescence intensity and lifetime (τ) versus viscosity (η) showed a linear relationship (FIGS. 2B and 2D).

In all, solvent data showed HC-1 directly senses solvent viscosity, responding through increases in quantum yield and fluorescence lifetimes. For molecular rotors, the relationship between fluorescence and viscosity is described by the Förster-Hoffmann equation where 'I' is steady-state fluorescence intensity, τ is fluorescence lifetime and η is the viscosity of the medium;

$$\log(I \text{ or } \tau) = A + B * \log(\eta)$$

HC-1 viscosity sensing can be adequately described by the Förster-Hoffmann equation. Plots showing the effect of viscosity on fluorescence intensity (R2~0.991) as well as lifetime (R2~0.939) reveal a linear relationship and show a very good correlation with the Forster-Hoffmann equation (FIGS. 2B and 2D). Therefore, HC-1 functions as molecular rotor that is responsive to viscosity. According to Forster-Hoffmann theory, the slope B relates to the nature of the molecular rotor with a B value ~0.6 for a perfect rotor. Fitting of the present experimental data revealed a B value of ~0.46 for HC-1 (FIG. 2B). This value is higher than previously reported B values for other dyes, and indicates that HC-1 is a very sensitive probe for viscosity.

Further, the results of effect of solvent viscosity on steady state fluorescence intensity of HC-2 is shown in FIG. 11A. It was observed that viscosity of the media was increased by adding increasing amount of glycerol in ethylene glycol-glycerol binary mixture.

Example 9

Time Resolved Fluorescence Study:

Time resolved fluorescence measurement was carried out using Horiba Scientifics fluorescence lifetime spectrometer (TemPro). Pulsed (1.4 ns FMHW). Nano-LED (560 nm) head was used as excitation source and single photon was detected at 610 nm in TCSPC mode. Lifetime data was extracted through Chi-square fitting into mono exponential decay using DAS6 analysis software, Horiba.

Figure 3D:
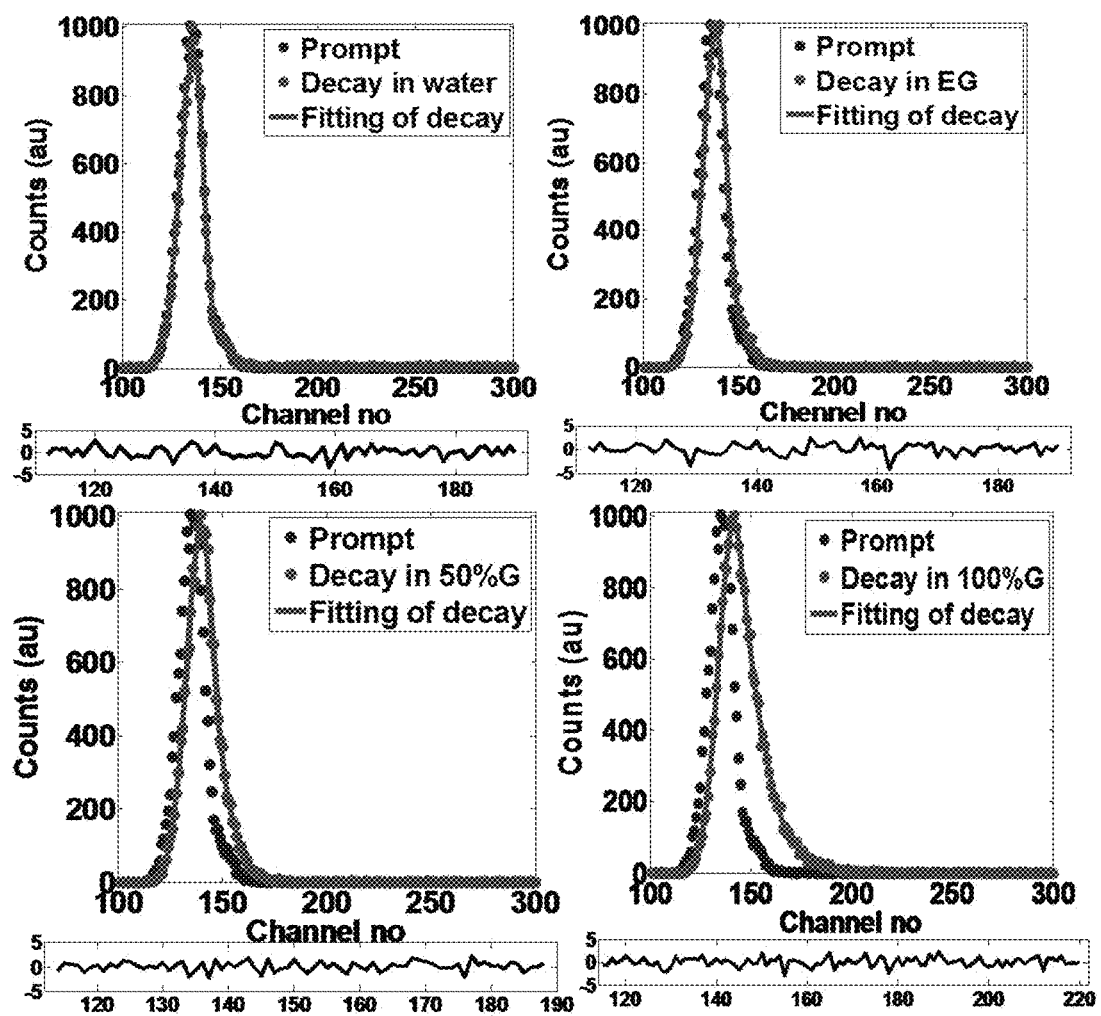
FIG. 3D: HC-1 is sensitive to local order and viscosity through changes in fluorescence lifetime. Time resolved fluorescence decay kinetics of HC-1 in solvents with different viscosity. X axis is the channel number where photon was detected, and each channel corresponds to 0.111767 ns. Y axis is the fluorescence counts of HC-1. Blue filled circles are for prompt response (IRF) and green filled circles are the fluorescence decay of HC-1 observed in different solvents. Red solid lines are the fitted line obtained from single exponential fitting. The residuals of fitting were given below each panel. The Chi-square value is ~1 and the residuals are random and do not follow any pattern, which confirms a good fitting.

The results of time resolved fluorescence decay kinetics of HC-1 in solvents with different viscosity is shown in FIG. 3D. X-axis is the channel number where photon was detected and each channel corresponds to 0.111767 ns. Y axis is the fluorescence counts of HC-1. Blue filled circles are for prompt response (IRF) and green filled circles are the fluorescence decay of HC-1 observed in different solvents. Red solid lines are the fitted line obtained from single exponential fitting. The residuals of fitting were given below the each panel. The Chi-square value is ~1 and the residuals are random and do not follow any pattern, which confirms a good fitting.

Example 10

Time Dependent Density Functional Theoretical (TD-DFT) Analysis:

All the computational calculations were carried out using Gaussian 09 program package. The ground state geometries of the Formula I dyes were optimized using DFT method, Becke's three parameter exchange function (B3) together with Lee-Yang-Parr (LYP) for non-local correlational basis set. Excited state geometries were optimized using CIS/6-311G (d) basis set as well as TDDFT-6-311G (d) basis sets. Experimentally observed values were in a better agreement when using the TDDFT optimized geometry. In order to get the information about absorption and emission properties, TDDFT calculations were carried out using the optimized geometries. Ground and excited state geometry optimizations and spectral calculations were carried out in both solution and gas phase. Solution phase calculations were carried out in water and in ethylene glycol medium using conductor like polarizable continuum model (CPCM) in the self-consistent reaction field (SCRF) theory.

Figure 15:
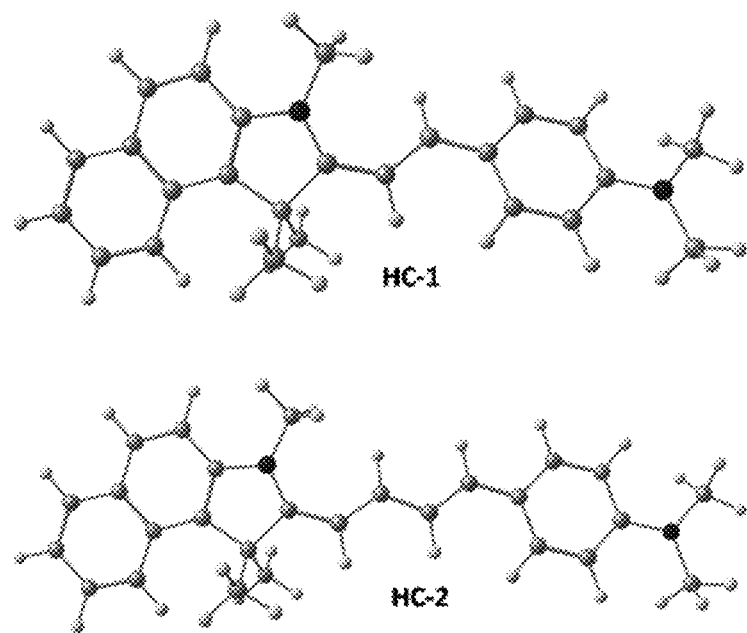
FIG. 15: Optimized ground state geometries of the HC-1 and HC-2 in the gas phase and solution phase using DFT/B3LYP/6–31+G (d) basis sets.

The ground state geometries of the HC-1 and HC-2 were optimized in the gas phase and solution phase using DFT/B3LYP/6-31+G (d) basis sets and are shown in FIG. 15. Using SCRF, the absorption transitions for HC-1 and HC-2 were calculated, with the three most allowed transitions reported in Table 2 below. TD-DFT calculations show that the transitions arising mainly from HOMO-LUMO show the highest oscillator strength [see FIGS. 3A, 3B].

Using ground state optimized geometry, the excited state geometries were optimized using two different basis sets CIS/6-311G (d) and TDDFT-6-311G (d). Then excited state transitions using TD-DFT calculations were carried out and found that results obtained from TD-DFT optimized geometries showed a good agreement with the experimental values. Results are shown in Tables 3 and 4. For excited state transition we also found that that there are three major transitions arising from excited state LUMO to HOMO. Along with calculating the wavelengths of electronic transitions, the oscillator strength associated with each transition was also calculated. In case of HC-1, the oscillator strength for both absorption and emission was higher in ethylene glycol compared to water, consistent with the experimental observations.

TABLE 2

Possible transitions obtained from Ground state optimized geometries of HC-1 and HC-2

| Molecule | Medium | $\lambda_{abs}$ in nm (calculated) | Oscillator strength (f) | Major contribution |
|---|---|---|---|---|
| HC-1 | Gas | 509.53106075 | 0.7771 | HOMO-LUMO (81%) |
| | | 430.321369611 | 0.7105 | HOMO-1->LUMO 73%) |
| | | 314.8005408461. | 0.0911 | HOMO->L + 1 (93%) |
| | Water | 497.189690068 | 0.4598 | HOMO->LUMO (96%) |
| | | 407.909830604 | 0.1764 | HOMO-1->LUMO 90%) |
| | | 333.6585834181. | 0.094 | HOMO->L + 1 (90%) |
| | Glycol | 502.57070536 | 1.4937 | HOMO->LUMO(96%) |
| | | 409.215766758 | 0.1678 | HOMO-1->LUMO(91%) |
| | | 333.568815444 | 0.0947 | HOMO->L + 1 (91%) |
| HC-2 | Gas | 538.402507656 | 1.4213 | HOMO-LUMO (85%) |
| | | 465.825792802 | 0.5996 | HOMO-1->LUMO(78%) |
| | | 330.562809641 | 0.0.1333 | HOMO->L + 1 (75%) |
| | Water | 534.43496556 | 1.535 | HOMO->LUMO(99%) |
| | | 438.091208834 | 0.0705 | HOMO-1->LUMO(92%) |
| | | 348.82872299 | 0.0649 | HOMO->L + 1 (96%) |
| | Glycol | 543.30846439 | 2.0815 | HOMO->LUMO(99%) |
| | | 439.519986572 | 0.0655 | HOMO-1->LUMO(93%) |
| | | 348.769847287 | 0.0651 | HOMO->L + 1 (96%) |

TABLE 3

Possible transitions obtained from excited state optimized geometries of HC-1 and HC-2 by TD-DFT method

| Molecule | Medium | $\lambda_{ems}$ in nm (TDDFT) optimized geometry | Oscillator strength (f) | Major contribution |
|---|---|---|---|---|
| HC-1 | Gas | 560.60470537 | 0.9673 | HOMO-LUMO (94%) |
|  |  | 441.426057035 | 0.6621 | HOMO-1->LUMO (86%) |
|  |  | 364.11070641 | 0.0402 | HOMO-2->L (90%) |
|  | Water | 562.486782686 | 0.4858 | HOMO->LUMO (94%) |
|  |  | 442.386843073 | 0.2459 | HOMO-1->LUMO (84%) |
|  |  | 364.646147583 | 0.0371 | HOMO-2->LUMO (90%) |
|  | Glycol | 568.418011368 | 1.0288 | HOMO->LUMO(95%) |
|  |  | 444.990799797 | 0.6324 | HOMO-1->LUMO(88%) |
|  |  | 365.775715835 | 0.0344 | HOMO-2->LUMO (95%) |
| HC-2 | Gas | 669.601083601 | 0.6739 | HOMO-LUMO (89%) |
|  |  | 503.322115209 | 1.1242 | HOMO-1->LUMO(75%) |
|  |  | 423.281337747 | 0.226 | HOMO-2->LUMO (82%) |
|  | Water | 552.145148128 | 1.5759 | HOMO->LUMO(99%) |
|  |  | 426.252941218 | 0.1108 | HOMO->LOMO 91%) |
|  |  | 339.710642004 | 0.06 | HOMO->L + 1 (95%) |
|  | Glycol | 626.843301681 | 2.102 | HOMO->LUMO(97%) |
|  |  | 480.965694156 | 0.6198 | HOMO-1->LUMO(90%) |
|  |  | 396.505601841 | 0.0109 | HOMO-2->LUMO (92%) |

TABLE 4

Possible transitions obtained from Excited state optimized geometries of HC-1 and HC-2 by CIS-6-311G method

| Molecule | Medium | $\lambda_{ems}$ in nm (CIS optimized geometry) | Oscillator strength (f) | Major contribution |
|---|---|---|---|---|
| HC-1 | Gas | 525.846946358 | 0.8258 | HOMO-LUMO (88%) |
|  |  | 430.605331199 | 0.6388 | HOMO-1->LUMO (76%) |
|  |  | 307.851698397 | 0.0816 | HOMO->L + 1 (82%) |
|  | Water | 513.1371286 | 0.4444 | HOMO->LUMO (97%) |
|  |  | 404.9918109760 | 0.232 | HOMO-1->LUMO (89%) |
|  |  | 325.366590595 | 0.0913 | HOMO->L + 1 (95%) |
|  | Glycol | 519.066369473 | 1.4781 | HOMO->LUMO(97%) |
|  |  | 406.412275911 | 0.2229 | HOMO-1->LUMO(90%) |
|  |  | 325.281228388 | 0.0928 | HOMO->L + 1 (95%) |
| HC-2 | Gas | 544.746014992 | 1.4697 | HOMO-LUMO (89%) |
|  |  | 455.63997285 | 0.6101 | HOMO-1->LUMO(79%) |
|  |  | 324.591441768 | 0.1082 | HOMO->L + 1 (40%) |
|  | Water | 552.145148128 | 2.102 | HOMO->LUMO(99%) |
|  |  | 426.252941218 | 0.1108 | HOMO-1->LUMO 91%) |
|  |  | 339.710642004 | 0.06 | HOMO->L + 1 (95%) |
|  | Glycol | 563.0743 | 2.1342 | HOMO->LUMO(99%) |
|  |  | 428.311523265 | 0.1029 | HOMO-1->LUMO(92%) |
|  |  | 340.053035215 | 0.0608 | HOMO->L + 1 (95%) |

Example 11

Preparation of Micelles:

Initially 300 mM solution of sodium dodecyl sulfate (SDS) in milli-Q water was prepared. Then, solution of varied concentrations (1-300 mM) by serial dilution was prepared. All the prepared solutions were heated at 70° C. for about 15 minutes and stored at room temperature overnight. Similarly, a stock of 10 mM was prepared for TritonX-100 also. Then solution of different concentration (0.05-4 mM) was prepared by serial dilution. Next day, HC-1 (final concentration 2.5 µM) was added to each solution and incubated for about 30 minutes and finally the fluorescence reading was measured.

The results can be observed in FIG. 4. FIG. 4 shows the change in fluorescence intensity with increasing concentration of Sodium Dodecyl Sulfate (SDS) [FIG. 4A] and TritonX-100 [FIG. 4B]. Data shows a clear point of inflexion with an increase in fluorescence intensity corresponding to micelle formation. Fitting of the fluorescence intensity versus concentration plots yielded critical micellar concentration (CMC) values of ~7.5 and ~1 mM for SDS and TritonX-100 (TX-100) respectively. These measured CMC values are comparable to reported values and shows that HC-1 is sensitive to aggregate formation. The data also reveals interesting new information about the local viscosity within the micelles. HC-1 reported a significantly larger increase in micro-viscosity associated with micelle formation for TritonX-100 (~7-fold fluorescence enhancement) as compared to SDS (~3-fold). Thus, HC-1 is a valuable probe for interrogating micro-viscosity in micro-heterogeneous media in new ways. Accordingly, the present disclosure describes interesting findings of micelle formation studies through a fluorescence micro-viscosity probe. These results are significant since micelles are a highly dynamic aggregates and HC-1 can report on micro-viscosity changes in these aggregates due to its high sensitivity.

Example 12

Imaging of Live Cell Mitochondria by HC-1, Co-Localization Assay of HC-1 Using MitoTracker Green and Effect of CCCP on HC-1:

Imaging of live cell mitochondria by HC-1: Human Bone Osteosarcoma Epithelial Cells (U2-OS cells) (ATCC® HTB96™) were cultured in McCoy's 5A media (from Hi-media # AT179) supplemented by 10% FBS (from Hyclone # SH30396.03) and Pen-Strep (Gibco #15140-122) according to ATCC instructions. For imaging, cells were plated on fibronectin coated (final concentration of 10 μg/ml) glass-bottomed dishes and allowed to attach. Prior to addition of dye(s), cells were washed with DPBS (Gibco, 14190-250) and incubated with 1 Mm HC-1 (final concentration) in serum free media for about 15 minutes at about 37° C. Cells were then washed twice with DPBS and fresh serum-free media was added.

Co-localization assay of HC-1 using MitoTracker Green: Cells were labeled using both MitoTracker Green and HC-1 dyes (by aforementioned protocol). Confocal images were taken using Olympus FV1000 Confocal microscope (×60 oil immersion objective at 1.6× optical zoom). Excitation parameters used were 488 nm excitation and 500-530 nm emission for MitoTracker Green, and 543 nm excitation and emissions above 560 nm for HCl. Pearson correlation dot plot was constructed using Coloc2 plugin of ImageJ.

Effect of Carbonyl Cyanide 3-Chloro Phenylhydrazone [CCCP]: Dye-labeled cells were imaged on the Olympus IX83 inverted microscope coupled to a 560 nm laser line connected to a Evolve 512 Delta EMCCD camera. 5 μM CCCP (final concentration) was used for the assay. Different regions were selected on the dish and imaged before the addition of CCCP and after addition at an interval of about 5 minutes for duration of about 15 minutes.

The results of the above studies are shown in FIG. 5. It is seen that HC-1 stains the mitochondria in live cells in a potential sensitive manner. Confocal fluorescence micrograph of live U2OS cells labeled with both MitoTracker Green [FIG. 5A] and HC-1 [FIG. 5B] & Merged image [FIG. 5C] as well as 2D intensity correlation (Pearson R: 0.95) dot plot [FIG. 5D] indicate colocalization of the dyes [also shown in FIG. 5H]. Scale bar: 20 μM. FIGS. 5E and 5F show the effect of CCCP on HC-1 fluorescence in U2OS cells—images acquired before [FIG. 5E] and after [FIG. 5F] addition of 5 μM CCCP (final concentration). CCCP causes loss of HC-1 fluorescence showing it is sensitive to mitochondrial membrane potential.

Example 13

Effect of Monensin on HC-1 and HC-2 Stained Mitochondria:

HC-1 labeled U2OS cells were imaged on the Olympus IX83 inverted microscope coupled to a 560 nm laser line connected to a Evolve 512 Delta EMCCD camera. 10 μM Monensin (final concentration) was used to check its effect on mitochondria. Different regions were selected on the dish and imaged at an interval of 30 minutes for duration of 1 hour. The effect of Monensin (10 μM) was also studied on HC-2 stained (250 nM) mitochondria of live HEK 293 cells after addition at 0 minute, 30 minutes, 60 minutes and 90 minutes.

The results of monensin effect on HC-1 labelled U2OS cells are shown in FIG. 6. It is seen that HC-1 is sensitive to changes in mitochondrial ordering. Gray scale images show the effect of Monensin on HC-1 fluorescence in mitochondria. Confocal images were acquired just after addition [0 mins—FIG. 6A]; after 30 minutes [FIG. 6B] and 60 minutes [FIG. 6C] of 10 μM Monensin. Further, quantitation of Monensin induced increase in fluorescence in specific regions of interest (ROIs) is shown in FIG. 6D (n=4). The four regions of interest (ROIs) chosen for analysis are marked in yellow (R1, R2, R3 and R4). Also, shown in FIG. 6E is a line-scan analysis of fluorescence intensity change on the addition of Monensin. The line across the cell used for quantitation is marked on the image in panel A (Scale bar: 20 μM).

The results of Monensin effect on HC-2 labelled HEK 293 cells is shown in FIGS. 11B and 11C. It is seen from FIG. 11B that there is a time-dependent increase in fluorescence intensity after addition of Monensin indicating that HC-2 also like HC-1 is sensitive to Monensin induced alteration in local ordering of mitochondria within live cells. FIG. 11C shows quantification and statistical analysis of the change in HC-2 fluorescence after addition of Monensin.

Example 14

Imaging HC-1 Stained Mitochondria of Embryonic Stem Cells (ESCs):

E14TG2a (mouse embryonic stem cells) were cultured in GMEM supplemented with FBS, Glutamine, Non-essential amino acids, β-mercaptoethanol, Penicilin-streptomycin and depending on culture conditions, with or without Leukemia Inducing Factor (LIF). Cells were plated on Matrigel® coated cover-slip dishes and allowed to adhere for about 36 hours before labeling them with HC-1 dye. Images were acquired on the FV1000 confocal microscope. Imaging set up used in the present example was same as the imaging set up used for colocalization described above.

For long term imaging of mitochondria in stem cells, cells were treated by 500 nM HC-1 for 30 minutes and washed by 1×PBS. Confocal (FV1000, Olympus) images were acquired for 12 hours at 3 hours interval. Same plate was used for long term imaging to check the cytotoxicity of HC-1.

Figures 7A, 7B, 7C:
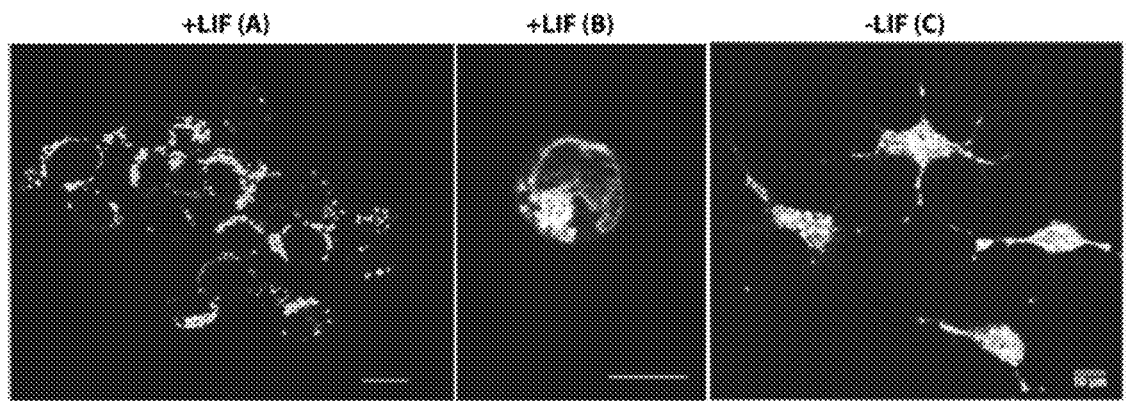
FIGS. 7A to 7C: Imaging mitochondria of embryonic stem cells (ESCs) and early differentiated cells using HC-1. Confocal images of HC-1 stained E14TG2a mouse ESCs either with Leukemia Inhibiting Factor (LIF) (A and B (zoomed)) or after LIF withdrawal (C). LIF-withdrawal causes spontaneous differentiation (C) whereas cells with LIF retain stemness (A and B). Scale bar: 10 µM.
Figure 8:
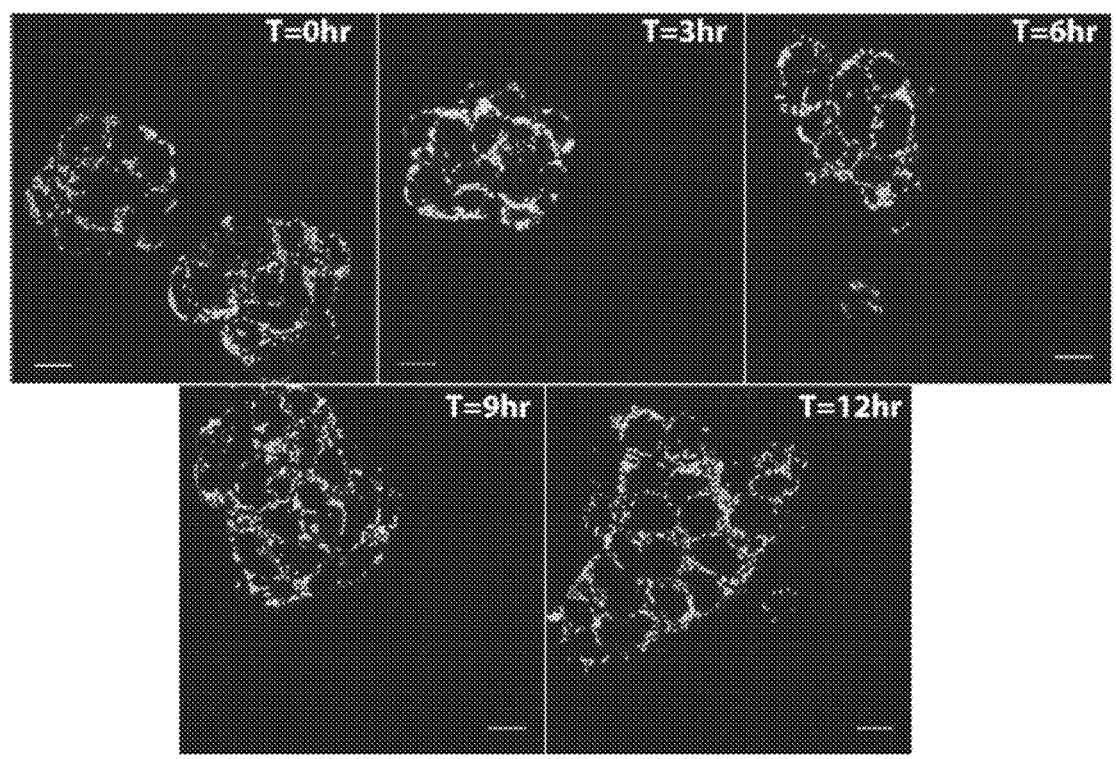
FIG. 8: HC-1 is suitable for long term imaging of mitochondria in embryonic stem cells (+LIF) with low toxicity. Confocal fluorescence micrographs were acquired at three hours interval up to twelve hours from the time of staining. Scale bar: 10 micron.
Figures 9A, 9B, 9C:
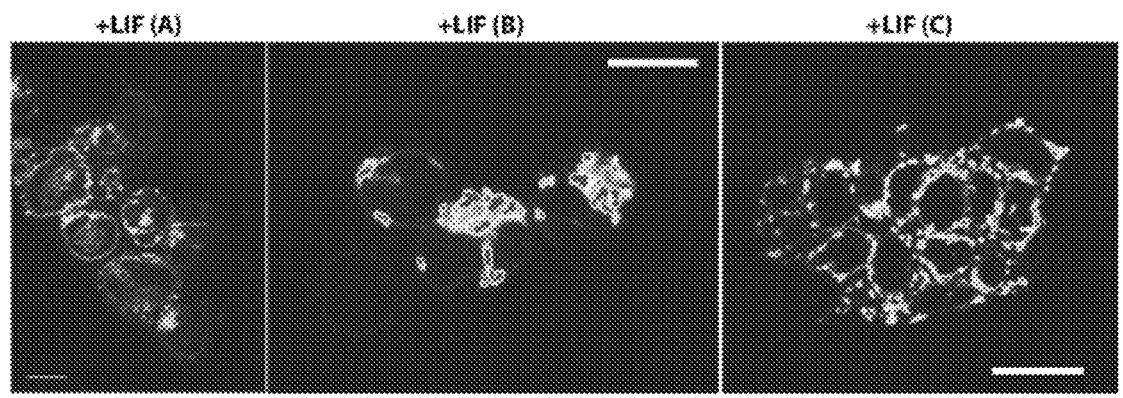
FIGS. 9A to 9C: Mitochondrial imaging of embryonic stem cells (ESCs) using HC-1. Confocal micrographs HC-1 stained mitochondria in live E14TG2a mouse embryonic stem cells. Stemness was maintained by addition of Leukemia Inhibitory Factor (LIF).
Figure 10:
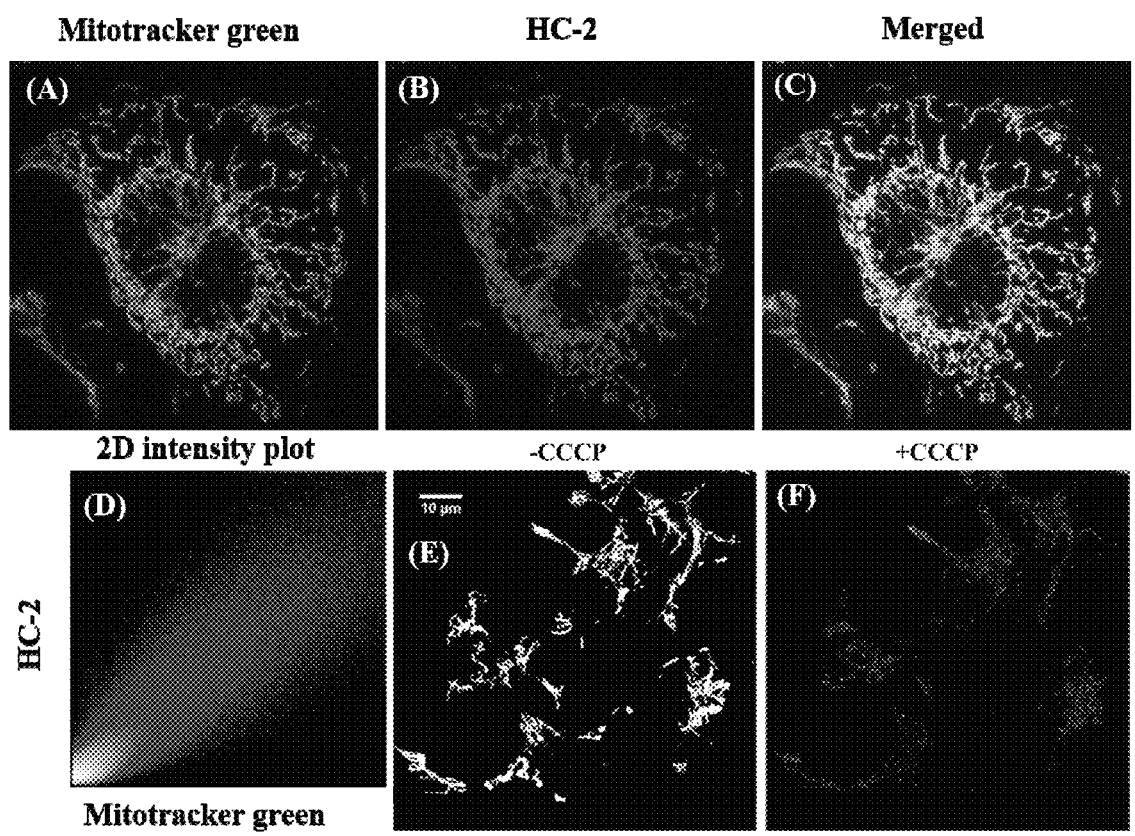
FIGS. 10A to 10F: HC-2 stains the mitochondria in live cells in a mitochondrial potential sensitive manner. Confocal fluorescence micrograph of live human primary fibroblast cells labeled with both MitoTracker Green (A) and HC-2 (B). Merged image (C) as well as 2D intensity correlation (Pearson R: 0.91) dot plot (D) indicates colocalization of the dyes. Scale bar: 20 micron. (E and F) Effect of Carbonyl Cyanide 3-Chloro Phenylhydrazone (CCCP) on HC-2 fluorescence in human embryonic kidney (HEK) cells. Images acquired before (E) and after (F) addition of 5 µM (final concentration) CCCP. CCCP causes loss of HC-2 fluorescence showing it is sensitive to mitochondrial membrane potential. Scale bar: 10 micron.

The results of the HC-1 imaging study on ESCs are provided in FIG. 7, FIG. 8 and FIG. 9. It is seen that HC-1 senses mitochondrial organization in ESCs and early differentiation. Particularly, FIG. 7 shows confocal images of HC-1 stained E14TG2a mouse ESCs either with Leukemia Inhibiting Factor (LIF) [FIG. 7A and FIG. 7B (zoomed)] or after LIF withdrawal [FIG. 7C]. LIF-withdrawal causes spontaneous differentiation (FIG. 7C) whereas cells with LIF retain stemness [FIG. 7A and FIG. 7B] (Scale bar: 10 μM).

Example 15

Photo-Toxicity Study During Repeat Photo-Illumination and Fast Mitochondrial Imaging HC-1 can be used for measuring mitochondrial mobility, dynamics and combination thereof. HC-1 can be used for fast imaging and repeated photo-illumination with low phototoxicity and minimal perturbation of mitochondrial function, in contrast to commercially available dyes.

The results of comparing the photostability of commercially known dye (TMRE) and HC-1 during fast imaging of mitochondria of live human primary fibroblasts was carried out. Fast (10 sec interval) time lapse images were acquired for 300 seconds. Upper panel (A, B and C) of FIG. 12 shows that TMRE photobleaches during fast imaging resulting in loss of mitochondrial fluorescence during time-lapse imaging. Whereas, HC-1 is significantly more photostable and suitable for fast imaging of mitochondria, repeat photo-illumination with high temporal resolution and measurement of mitochondrial mobility, dynamics and combinations thereof.

Example 16

Mitochondrial Imaging of Live Pluripotent Stem Cells

Figure 13:
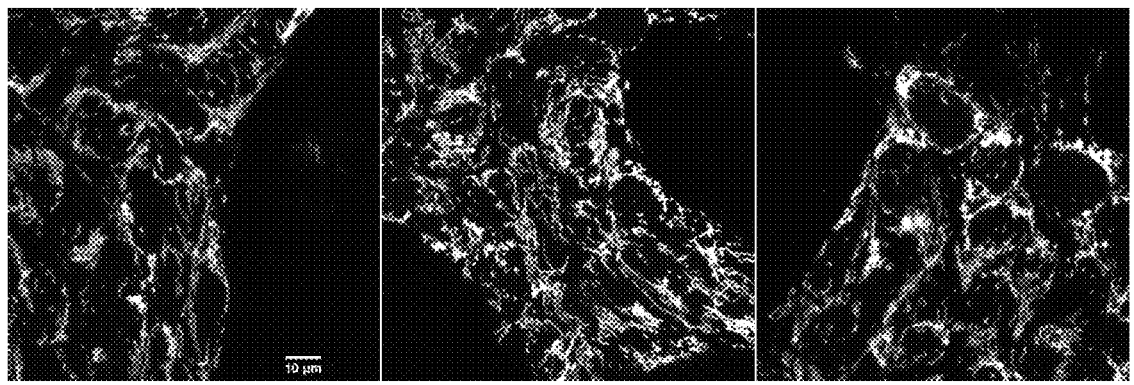
FIG. 13: HC-1 and HC-2 stained mitochondria of human pluripotent stem cells (hPSCs). Cells were treated either with HC-1 (upper panel) or HC-2 (lower panel). These are the 2D projections of Z-stacked images. Images confirm uniform staining of the mitochondria of live hPSCs.
Figure 13:
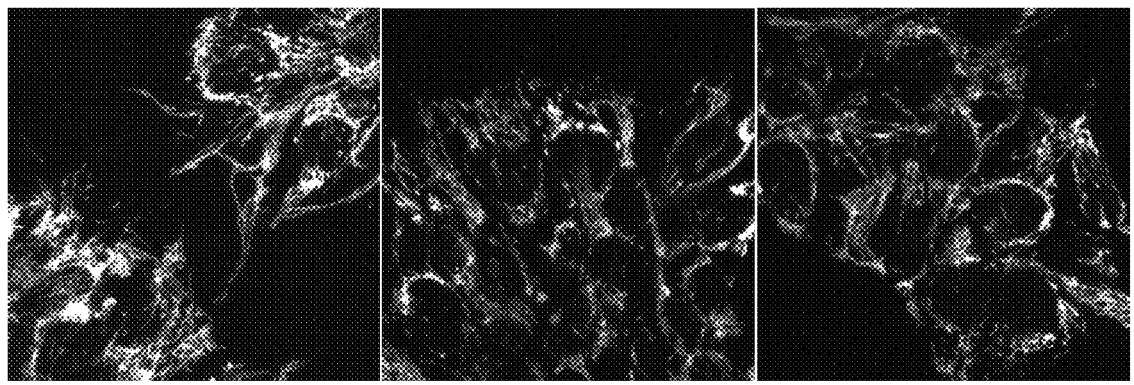

HC-1 and HC-2 are suitable for mitochondrial imaging of live human pluripotent stem cells. For imaging of mitochondria of live human pluripotent stem cells, HC-1 and HC-2 (250 nM) were contacted with live human pluripotent stem cells (hPSCs) for 30 minutes, washed with excess media and then imaged using confocal fluorescence microscopy. The results showed that HC-1 and HC-2 are capable of said mitochondrial imaging in human pluripotent stem cells (FIG. 13).

Example 17

Imaging Local Order and Viscosity of Mitochondria and Measuring Cellular State & Function A study on the use of HC-1 for imaging local order and viscosity of mitochondria and use of said imaging to measure changes in mitochondrial function and cellular state and function was carried out. Here, HC-1 imaging of local ordering of mitochondria was used to estimate changes in cell function, state and heterogeneity during activation of primary mouse fibroblasts, in cellular models of fibrosis.

The results of the imaging of the HC-1 stained mitochondria during activation of primary mouse fibroblasts is provided in FIG. 14. Cellular heterogeneity and cell state during activation can be probed in terms of mitochondrial order by multiparametric imaging using HC-1 (250 nM) and TMRE (125 nM). HC-1 imaging data revealed the heterogeneity in terms of local ordering (microviscosity) of the mitochondria in different sub-populations of cells stained with distinct markers, CD26 and Sca-1.

Accordingly, the present disclosure is successful in providing dyes (compound of Formula I) which have advantages including but not limiting to the following:
a) are useful for uniform staining of primary cells and stem cells, including embryonic stem cells and induced pluripotent cells;
b) are useful for uniform staining and imaging of stem cells, including human pluripotent and human embryonic stem cells;
c) are retained in the stem cells and are not exported;
d) are photostable allowing multiple light exposures and repeated imaging without photo-damage of the mitochondria. This allows long-term and repeat imaging of sensitive cells like primary cells and stem cells;
e) are useful for fast tracking of mitochondria and map of out mitochondrial mobility in live cells with very high temporal resolution, without perturbing mitochondrial function and segregation;
f) are sensitive to local ordering and micro-viscosity (which helps in providing new information on mitochondrial microenvironment), apart from mitochondrial potential;
g) are useful for multiparametric imaging of mitochondria, which helps in investigating mitochondrial changes in cellular models of human disease, including fibrosis, Alzheimer's disease and cardiac diseases;
h) have a longer shelf-life and are easy to store (4° C.);
i) emit at long wavelengths (~600 nm or longer) that makes it easy to image thick samples and suitable for uniform staining of the human PSCs;
j) are highly photostable in comparison with the commercially available dyes;
k) have low toxicity and generate little or no reactive species upon long term light irradiation compared to the commercially available dyes;
l) are suitable for long-term imaging of stem cells and prevent toxicity-induced differentiation. This is very critical since current dyes have a tendency to cause unwanted differentiation of stem cells. The present dyes are superior for low-perturbation staining and imaging of stem cells;
m) are sensitive to local ordering of the mitochondria and hence it is possible to probe cellular heterogeneity in terms of the status of the mitochondria. Cell heterogeneity complicates analysis of cellular models of human diseases. Therefore, easy study of cell heterogeneity using cell-permeable probes is advantageous.

The invention claimed is:

1. A method of imaging mitochondria in eukaryotic cells, tissues or animals comprising: contacting the eukaryotic cells, tissues or animals with compound of Formula I to stain the mitochondria and imaging the mitochondria, wherein the compound of Formula I

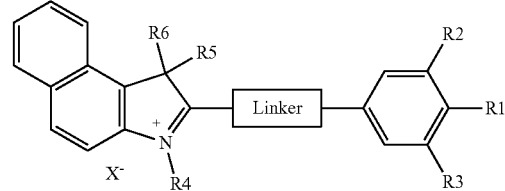

Formula I wherein,
'R1' is selected from a group consisting of hydrogen, dialkyl amino, diaryl amino and alkoxy;
'R2', 'R3', 'R4', 'R5' and 'R6' are individually selected from a group consisting of hydrogen, alkoxy and alkyl;
'X' is selected from a group consisting of I, Cl, Br and F; and
'Linker' is selected from a group consisting of alkenylene moiety (CH=CH), alkadienyl group (—CH=CH—CH=CH—).

2. The method as claimed in claim 1, wherein the imaging is fluorescence imaging.

3. The method as claimed in claim 1, further comprising sensing local ordering or viscosity of the mitochondria, tracking the mitochondrial mobility, and dynamics or combinations thereof.

4. The method as claimed in claim 3, wherein the sensing of said local ordering or viscosity is performed by measuring fluorescence intensity, fluorescence life time, or a combination thereof.

5. The method as claimed in claim 4, further comprising evaluating mitochondrial function by said sensing of the local ordering or viscosity of the mitochondria.

6. The method as claimed in claim 3, wherein the tracking of mitochondrial mobility and dynamics is performed by time-lapse imaging using repeated photo illumination.

7. The method as claimed in claim 3, further comprising evaluating a state, a function, or a combination thereof of the cells or tissues by said mitochondrial imaging.

8. The method as claimed in claim 7, further comprising identifying or screening a disease condition by evaluating changes in said state, function or a combination thereof of said cells or tissues.

9. The method as claimed in claim 1, wherein the eukaryotic cells are live primary cells, induced pluripotent cells (iPCs) or a combination thereof; wherein the eukaryotic cells are from human origin, mouse origin or other animal origin; and wherein the eukaryotic cells are selected from a group consisting of cells in culture, cultured cells, cells from tissue and combinations thereof.

10. The method as claimed in claim 9, wherein the live primary cells are selected from a group consisting of fibroblast cells, stem cells and a combination thereof; wherein the stem cells are selected from a group consisting of embryonic stem cells, adult stem cells and a combination thereof; and wherein the induced pluripotent cells (iPCs) are selected from a group consisting of human induced pluripotent stem cells (hiPSCs), mouse induced pluripotent stem cells (miPSCs), induced pluripotent stem cells from any other animal and combinations thereof.

11. The method as claimed in claim 1, wherein the method of imaging mitochondria in the eukaryotic cells comprises:
 a) contacting the cells with the compound of Formula I by adding a cell culture medium containing the compound to the cells,
 b) incubating the cells for a time-period ranging from about 5 minutes to about 48 hours,
 c) optionally, washing off the excess compound and adding a fresh cell culture media, to obtain stained cells, and
 d) imaging the stained cells by fluorescence microscope.

* * * * *